(12) United States Patent
Sinderby et al.

(10) Patent No.: US 12,741,111 B2
(45) Date of Patent: Sep. 22, 2026

(54) METHOD AND SYSTEM FOR CONTROLLING A LEVEL OF VENTILATORY ASSIST APPLIED TO A PATIENT BY A MECHANICAL VENTILATOR

(71) Applicants: Christer Sinderby, Ontario (CA); Jennifer Beck, Toronto (CA); Norman Comtois, Scarborough (CA)

(72) Inventors: Christer Sinderby, Ontario (CA); Jennifer Beck, Toronto (CA); Norman Comtois, Scarborough (CA)

(73) Assignee: UNITY HEALTH TORONTO, Toronto (CA)

(*) Notice: Subject to any disclaimer, the term of this patent is extended or adjusted under 35 U.S.C. 154(b) by 1050 days.

(21) Appl. No.: 17/910,102

(22) PCT Filed: Mar. 5, 2021

(86) PCT No.: PCT/CA2021/050297
§ 371 (c)(1),
(2) Date: Sep. 8, 2022

(87) PCT Pub. No.: WO2021/179066
PCT Pub. Date: Sep. 16, 2021

(65) Prior Publication Data

US 2023/0113361 A1 Apr. 13, 2023

Related U.S. Application Data

(60) Provisional application No. 62/987,265, filed on Mar. 9, 2020.

(51) Int. Cl.
*A61M 16/00* (2006.01)
*A61B 5/087* (2006.01)

(52) U.S. Cl.
CPC .......... *A61M 16/024* (2017.08); *A61B 5/087* (2013.01); *A61M 2016/0027* (2013.01); *A61M 2016/0039* (2013.01)

(58) Field of Classification Search
CPC ........ A61M 16/024; A61M 2016/0027; A61M 2016/0039; A61M 16/026; A61M 16/06;
(Continued)

(56) References Cited

U.S. PATENT DOCUMENTS 3,480,006 A * 11/1969 Schomber .............. A61B 5/087 600/533
5,820,560 A 10/1998 Sinderby et al.
(Continued)

FOREIGN PATENT DOCUMENTS

WO 2017/113017 A1 7/2017

OTHER PUBLICATIONS

Extended European Search Report issued on Feb. 15, 2024 by the EPO in connection with EP patent application No. 21768476.0, 8 pages.

(Continued)

*Primary Examiner* — Brandy S Lee
*Assistant Examiner* — Tina Zhang
(74) *Attorney, Agent, or Firm* — BCF LLP

(57) ABSTRACT

A first respiratory volume of the patient is determined during at least a part of the under-assisted breath. A second respiratory volume of the patient is determined during at least a part of the assisted breath, for a duration matching the part of the under-assisted breath. The first and second respiratory volumes may be measured for a same value of a neural respiratory drive of the patient. A volume assistance correction is calculated based on the first and second respiratory volumes. A pressure is measured at the mechanical ventilator or at an airway of the patient. A load of the respiratory (Continued)

system of the patient is calculated based on the volume assistance correction and on the measured pressure. The mechanical ventilator is controlled according to the load of the respiratory system of the patient and may implement a prediction for back-up use when the patient is not spontaneous breathing.

35 Claims, 17 Drawing Sheets

(58) Field of Classification Search
CPC .......... A61M 16/0066; A61M 2230/60; A61M 2230/005; A61B 5/087; A61B 5/091; A61B 5/389; A61B 5/113; A61B 5/349; A61B 5/395; A61B 5/40; A61B 5/4836
USPC ............ 128/204.23, 204.21, 204.18, 200.24, 128/204.26
See application file for complete search history.

(56) References Cited

U.S. PATENT DOCUMENTS 6,588,423 B1 7/2003 Sinderby
8,720,441 B2 5/2014 Sinderby
9,179,861 B2 11/2015 Sinderby et al.
10,517,528 B2 12/2019 Sinderby
2004/0118403 A1* 6/2004 O'Connor ......... A61M 16/0069 128/204.23
2007/0151563 A1 7/2007 Ozaki
2008/0121231 A1* 5/2008 Sinderby .............. A61B 5/6853 600/587
2010/0228142 A1 9/2010 Sinderby
2012/0006327 A1* 1/2012 Sinderby ........... A61M 16/0051 128/204.23
2012/0103334 A1* 5/2012 Sinderby ................ A61B 5/389 128/204.18
2014/0123979 A1* 5/2014 Doyle .................... G16H 50/20 128/204.23
2016/0220783 A1* 8/2016 Garcia Molina ..... A61M 21/02
2017/0128684 A1 5/2017 Sinderby et al.
2019/0015615 A1 1/2019 Sinderby et al.
2019/0029547 A1* 1/2019 Watarai ................ A61B 5/6892
2019/0175908 A1* 6/2019 Thakkar ............... A61B 5/4519

OTHER PUBLICATIONS

International Search Report of PCT/CA2021/050297, Search Completed on May 11, 2021, Authorized Office: Alan Jones, 3 pages.

* cited by examiner

Figure 7D:
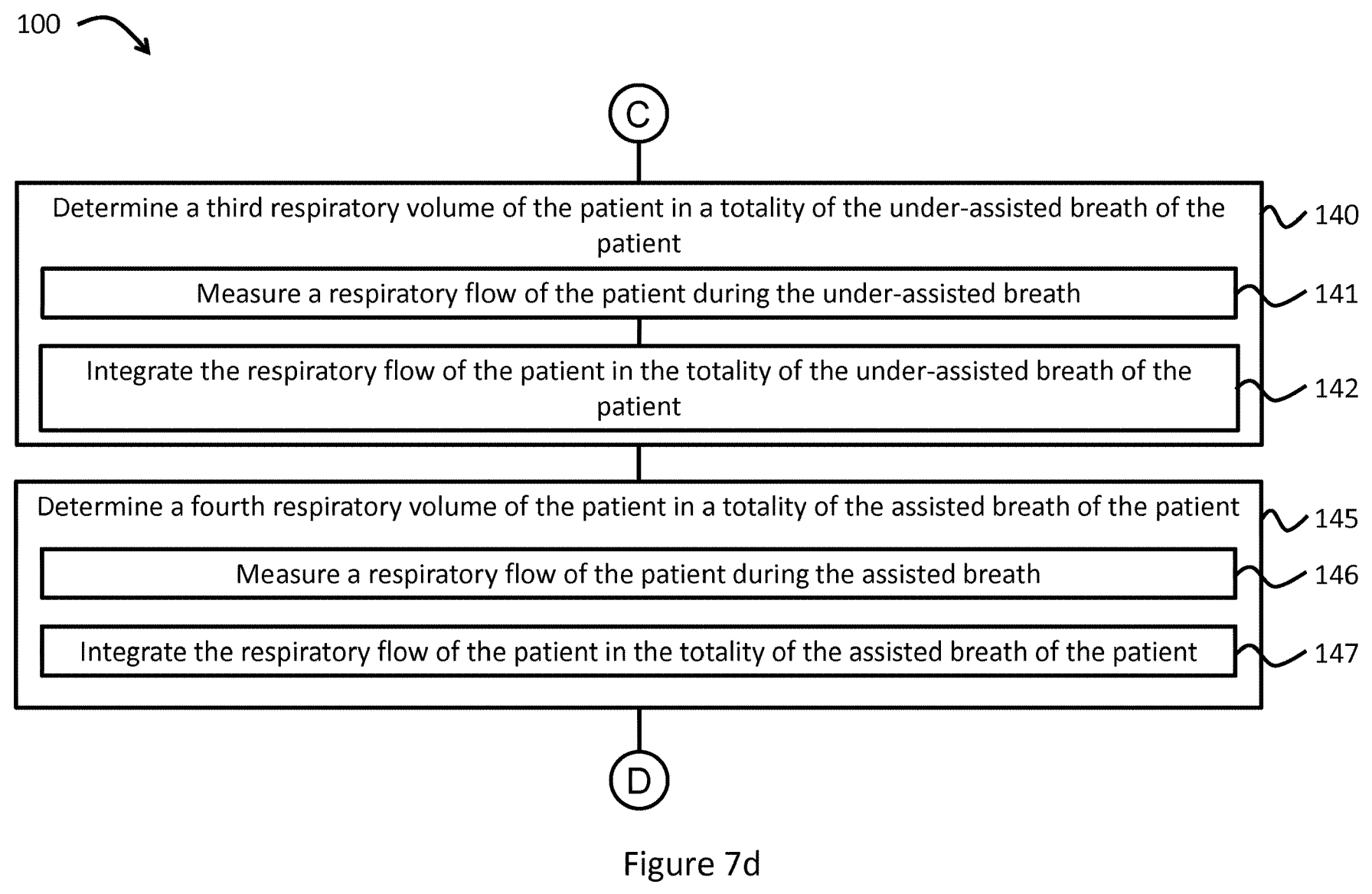

140 Determine a third respiratory volume of the patient in a totality of the under-assisted breath of the patient 141 Measure a respiratory flow of the patient during the under-assisted breath 142 Integrate the respiratory flow of the patient in the totality of the under-assisted breath of the patient 145 Determine a fourth respiratory volume of the patient in a totality of the assisted breath of the patient 146 Measure a respiratory flow of the patient during the assisted breath 147 Integrate the respiratory flow of the patient in the totality of the assisted breath of the patient

METHOD AND SYSTEM FOR CONTROLLING A LEVEL OF VENTILATORY ASSIST APPLIED TO A PATIENT BY A MECHANICAL VENTILATOR

CROSS-REFERENCE

The present application claims priority from U.S. Provisional Application Ser. No. 62/987,265, filed on Mar. 9, 2020, the disclosure of which is incorporated by reference herein in its entirety.

TECHNICAL FIELD

The present disclosure relates to the field of ventilatory assist technologies. More specifically, the present disclosure relates to a method and a system for controlling a level of ventilatory assist applied to a patient by a mechanical ventilator.

BACKGROUND

Mechanical ventilation has for a long time been a cornerstone in treatment of patients with acute respiratory failure. Traditionally, mechanical ventilators delivered assist of predetermined magnitude and frequency to maintain adequate ventilation, according to a so-called controlled mode ventilation (CMV). CMV left little room for the patients to be spontaneously breathing. One important advantage of using CMV in patients without active breathing efforts is that pressure, flow, and volume measurements allow to determine respiratory system mechanics of the patients, such as elastic, resistive and total respiratory system loads. This information is very important for determining the degree and progress of underlying pathology. CMV modes include for example volume control ventilation (VCV), used to deliver a preset flow to a target volume, and pressure control ventilation (PCV), used to deliver a constant pressure. Both VCV and PCV operate under fixed time cycling.

Over the last decades, progressively reduced use of sedatives has increased the occurrence of spontaneous breathing in patients who need mechanical ventilation, calling for algorithms that initiate and terminate the ventilators assist in synchrony with the patient's inspiration. Todays' focus is developing towards use of CMV during acute treatments at admission, following with transition to so called partial ventilatory assist (PVA) in subacute stages where the patient and mechanical ventilator share the effort to overcome inspiratory load. A goal of PVA is to synchronize and integrate assist delivery to the patient's breathing efforts, providing efficient assist while preventing the patient from "fighting the ventilator" or, in other words, being agitated by the ventilator. Further advantage of PVA is that the respiratory muscles are conditioned, preventing degeneration and hypotrophy of the breathing muscles.

A most common "triggered and cycled" mode is called pressure support ventilation (PSV), which delivers a fixed target pressure and is traditionally controlled by pneumatic signals measured in the respiratory circuit between the mechanical ventilator and the airways of the patient. PSV uses pressure, flow, and/or volume to initiate a breath cycle, followed by the relative reduction in inspiratory flow to guide termination of assist at the end of the breath cycle. Hence, when breathing is synchronized to the ventilator assist in PSV, the patient can alter his/her contribution, whereas the ventilator cannot. As such, the relative contribution of the patient can vary over time.

Modern modes of mechanical ventilation have expanded the time dependent synchrony of assist delivery to also satisfy intra-breath demand by adjusting the magnitude of assist in proportion to inspiratory efforts of the patients. Hence, the mechanical ventilatory assist can be synchronized with inspiratory efforts in patients with acute respiratory failure who actively participate in inspiration while receiving mechanical ventilatory assist.

The patient's respiratory function and the load of breathing needs to be assessed in order to adequately adjust the mechanical ventilatory assist. Traditionally, determination of the mechanics of the patient's respiratory system has been performed during patient's respiratory muscle inactivity. Such inactivity was, for example, induced by deep sedation and hyperventilation or paralysis, allowing the mechanical ventilator to apply pressure to the patient's respiratory system in order to inflate the patient's lungs without contribution from the respiratory muscles. The obtained data was presented as dynamic pressure/volume curves showing the pressures required to inflate the patient's respiratory system. The pressure/volume curves were used to describe dynamic mechanics of the patient's respiratory system, such as compliance expressed in ml/cm$H_2O$, or elastance expressed in cm$H_2O$/ml, as well as resistance expressed in cm$H_2O$/ml/s.

Unfortunately, traditional measurements of respiratory system mechanics in mechanically ventilated patients that actively participate in inspiration introduces an error since the inspiratory volume generated by the patient appears in the volume measurement while the pressure of the patient is not available unless pressure sensors, for example esophageal catheter pressure sensors, are introduced into the patient's respiratory system to measure lung distending pressure. This measurement is imprecise because it does not include the patient's effort used to expand the chest wall, including the patient's ribcage and abdomen. Hence, in the absence of measurements of the pressure contribution of the patient's respiratory muscles, the larger the patient's own inspiratory volume generation the larger the error of the measured pressure/volume curve.

The patient's neural activation of respiratory muscles reflects the force applied by the respiratory muscles. Hence, if two non-assisted breaths (i.e. without mechanical ventilation) have the same neural activation they should provide the same inspiratory volume. If mechanical ventilation is applied to one of the two breaths with the same neural activation, the assisted breath will provide inspiratory pressure generated by the mechanical ventilator and its inspiratory volume will be increased compared to the non-assisted breath. Given that both breaths have the same neural activation, one can assume that the force to expand the patient's respiratory system and inflate the lungs was similar during both breaths. It should however be reminded that some effects on force generation occur during assisted breath due to change in lung volume affecting muscle length/tension and added flow assist affecting force/velocity relationship.

International Patent Publication no. WO 2017/113017 A1, published on Jul. 6, 2017 to Sinderby et al. (hereinafter "Sinderby'017"), the disclosure of which being incorporated by reference herein, describes taking advantage of neural activation, using for example diaphragm electrical activity (EAdi), the diaphragm being the main respiratory muscle. Sinderby'017 demonstrates a method using comparing breaths with assist (including patient and ventilator contributions) and breaths without assist (only including patient contributions) that had matching EAdi patterns, evidenced by the same neural activation of respiratory muscles in both assisted and non-assisted breaths. The disclosed method subtracts a volume generated by the patient during the non-assisted breath from a volume generated during the assisted breath. The residual volume is used to generate a dynamic pressure-volume curve using the pressure generated by the ventilator during the assisted breath. The pressure-volume curves are based on the so-called neurally adjusted ventilatory assist (NAVA) mechanical ventilatory assist mode as described in U.S. Pat. No. 5,820,560, issued on Oct. 13, 1998 to Sinderby et al. (hereinafter "Sinderby'560"), the disclosure of which being incorporated by reference herein. NAVA not only synchronizes the operation of the mechanical ventilator with patient's inspiratory effort, but also controls the mechanical ventilator to deliver positive assist pressure in proportion to electrical activity of a patient's respiratory muscle, for example the patient's EAdi. Specifically, the magnitude of the pressure assist supplied by the mechanical ventilator to the patient is adjusted by a gain factor that converts the electrical activity of the patient's respiratory muscle, for example EAdi, into an assist pressure level; this gain factor is the so-called NAVA level.

Using NAVA to calculate the respiratory system pressure/volume curve by removing the patient's inspiratory volume generation during the non-assisted breath from that of the assisted breath and plotting it against the measured pressure assist generated by the ventilator provides a trustworthy pressure/volume curve or relationship to describe the patient's respiratory system load and allows to determine the mechanical pressure and EAdi required to inflate the patient's respiratory system to a given inspiratory volume.

When measuring the dynamic respiratory mechanics during a mode that provides proportional assist to the patient effort, the ventilator delivers a level of assist that corresponds to the contribution of the patient. Increasing the assist results in higher rate of increase in ventilator pressure relative to patient, so that the ventilator volume contribution increases with increasing proportional assist.

Mechanical ventilators go into back-up mode when patients are no longer spontaneously breathing (lost EAdi). Conventional mechanical ventilators use arbitrarily assigned control parameters when in back-up mode.

Studies were made to test the teachings of Sinderby'017 on non-proportional assist modes. EAdi was used to trigger and terminate PSV assist in synchrony with neural inspiratory breath cycles, so that PSV was synchronized to patient's neural timing of inspiratory efforts. The same pressure assist was delivered throughout inspiration, so that the assist was not proportional to the efforts of the patients. The dynamic respiratory mechanics of the patients were evaluated during paralysis. In contrast with findings obtained when using NAVA, use of PSV failed to predict a trustworthy pressure/volume curve or relationship to describe the patient's respiratory system load and to determine the mechanical pressure. The EAdi required to inflate the patient's respiratory system to a given inspiratory volume during PSV could not be reliably predicted. Without reliable evaluation of the respiratory mechanics of the patients, control of a mechanical ventilator in PSV mode cannot be as accurate as when in NAVA mode.

Regardless, PSV is still a viable option for providing ventilatory assist to a patient. However, the lack of reliable evaluation of the respiratory mechanics of the patients when delivering assist in PSV mode limits the accuracy of control of delivery assist to the patients.

Therefore, there is a need for improvements in ventilatory assist systems that compensate for problems related to limits to the accuracy of control of delivery assist to patients.

SUMMARY

According to the present disclosure, there is provided a method for controlling a level of ventilatory assist applied to a patient by a mechanical ventilator. A first respiratory volume of the patient is determined during at least a part of the under-assisted breath of the patient. A second respiratory volume of the patient is determined during at least a part of the assisted breath of the patient for a duration matching the at least a part of the under-assisted breath of the patient. A volume assistance correction is calculated based on the first and second respiratory volumes. A pressure is measured at the mechanical ventilator or at an airway of the patient. A load of the respiratory system of the patient is calculated based on the volume assistance correction and on the pressure at the mechanical ventilator or at the airway of the patient. The mechanical ventilator is controlled according to the load of the respiratory system of the patient.

According to the present disclosure, there is also provided a system comprising a determiner, a pressure sensor and a controller. The determiner determines a respiratory volume delivered to the patient. The pressure sensor is adapted for measuring a pressure at a mechanical ventilator or at an airway of the patient. The controller is operatively connected to the determiner, and to the pressure sensor. The controller comprises a processor and a non-transitory computer-readable medium. The computer-readable medium has stored thereon machine executable instructions for performing, when executed by the processor, a method for controlling a level of ventilatory assist applied to the patient by the mechanical ventilator.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIGS. 7*a*-7*e* are a sequence diagram showing operations of a method for controlling a level of ventilatory assist applied to a patient by a mechanical ventilator;

Like numerals represent like features on the various drawings.

DETAILED DESCRIPTION

Various aspects of the present disclosure generally address one or more of the problems to limits to the accuracy of control of delivery assist to patients.

The present disclosure describes a new method and a new system to resolve the limited accuracy of control of delivery assist during both pressure support ventilation (PSV) and neurally adjusted ventilatory assist (NAVA).

Generally speaking, the present technology synchronizes respiratory assist provided by a mechanical ventilator with a neural respiratory drive (or respiratory effort) of the patient. Respiratory volumes of the patient are considered both during at least one under-assisted breath and during assisted breaths. A pressure measurement reflecting a pressure contribution from the mechanical ventilator is obtained at the mechanical ventilator or at an airway of the patient. A volume assistance correction is calculated based on these respiratory volumes. A load of the respiratory system of the patient is calculated based on this pressure measurement and on the volume assistance correction. Control of the mechanical ventilator is altered based on the load of the respiratory system. In the context of the present disclosure, an under-assisted breath may include a non-assisted breath, in which the mechanical ventilator provides no pressure contribution to the patient. An under-assisted breath may alternatively include a partially-assisted breath in which the mechanical ventilator provides a limited pressure contribution less than in the case of an assisted breath.

In more details, the present technology adjusts the respiratory volume of the patient during an assisted breath to provide an accurate pressure to volume relationship during that assisted breath. This pressure to volume relationship describes a load of the respiratory system during a spontaneous inspiration with mechanical ventilator assist. A calculation provides a corrected volume during the assisted breath. This correction is based on a relative difference between assisted and under-assisted breaths. Details of the calculation of the corrected volume are provided hereinbelow. The load of the respiratory system of the patient is calculated by dividing the pressure contribution from the mechanical ventilator measured at the mechanical ventilator or at the airway of the patient by the corrected volume. This calculation of a pressure to volume relationship defines the load of the respiratory system of the patient. This knowledge of respiratory features of the patient may be used to control the mechanical ventilator in view of reaching various performance goals.

Figure 1:
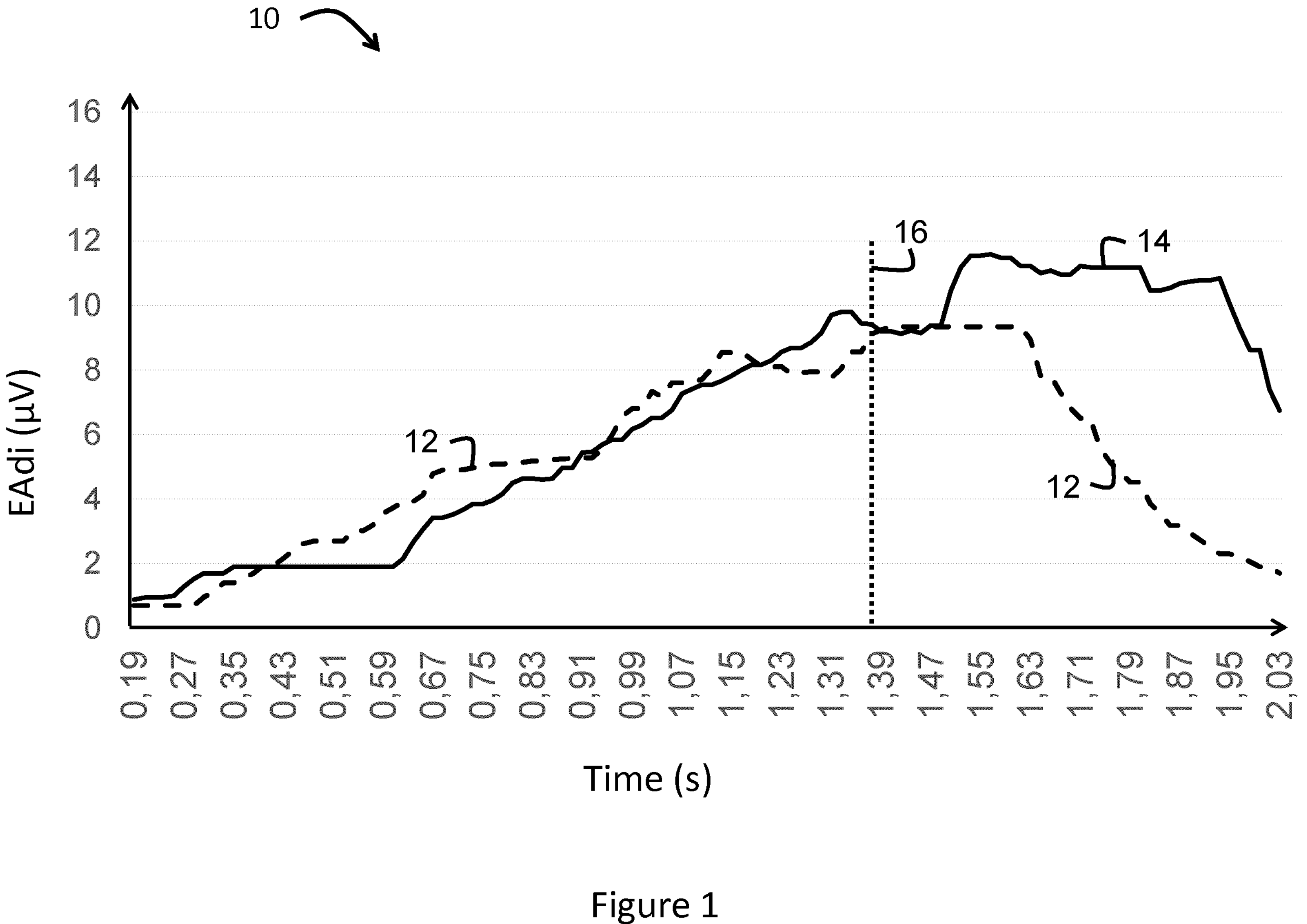
FIG. 1 is a graph showing an example of EAdi measurements during a non-assisted breath and during a proportionally assisted breath of a patient.

Referring now to the drawings, FIG. 1 is a graph showing an example of EAdi measurements during a non-assisted breath and during a proportionally assisted breath (NAVA mode) of a patient. In a graph 10, a curve 12 shows a variation of the diaphragm electrical activity (EAdi) of the patient over time, over the course of a non-assisted breath. A curve 14 shows a variation of the diaphragm electrical activity (EAdi) of the patient over the course of breath assisted by NAVA. The curves 12 and 14 are shown over a time scale so that the onset of inspiration occurs at the same time. The curves 12 and 14 are well-correlated until one of the curves 12 and 14 arrives first at an EAdi peak at a time 16, which is a peak of the EAdi for the non-assisted breath in the example of FIG. 1. The curves 12 and 14 are less correlated thereafter.

Figure 2:
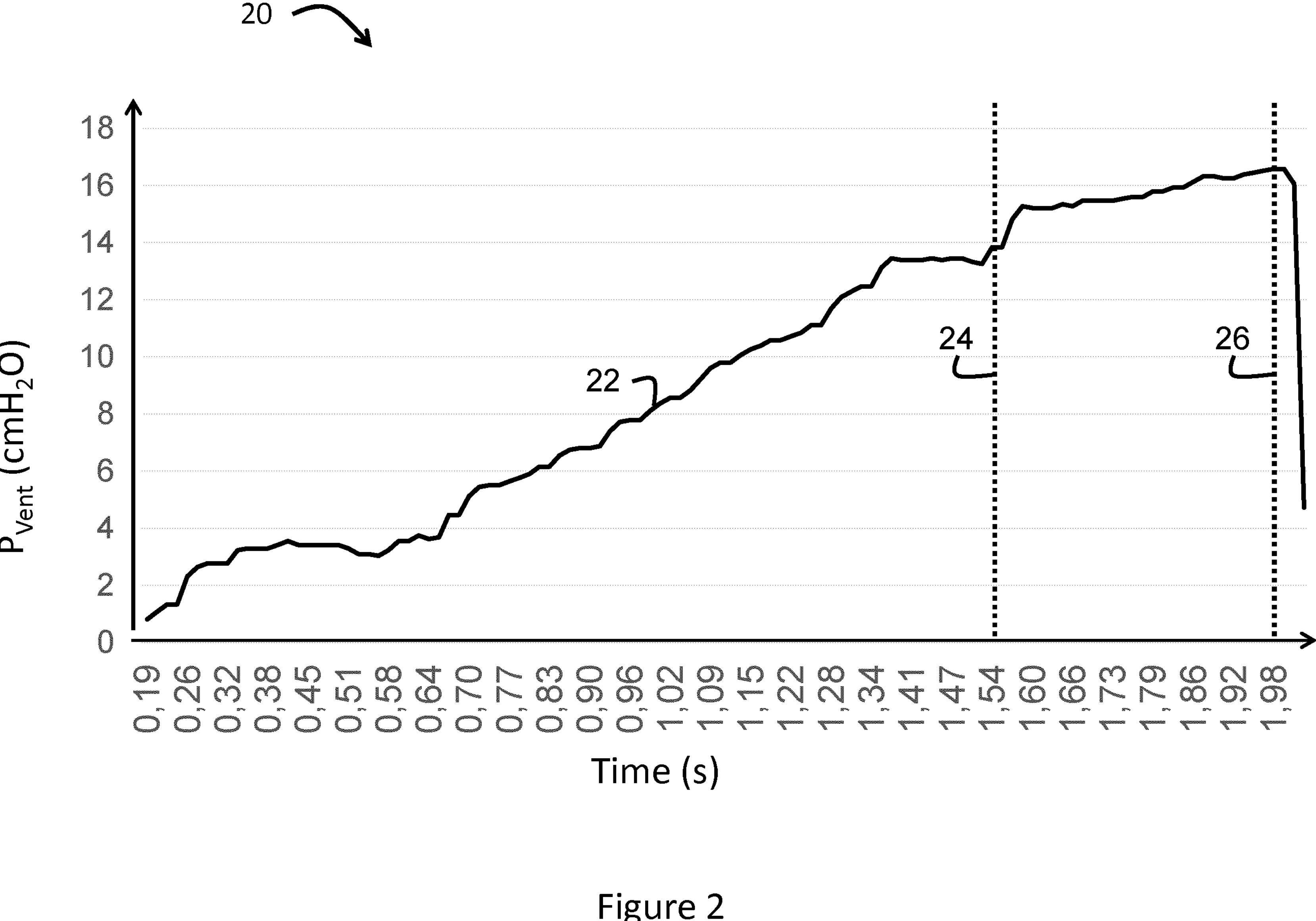
FIG. 2 is a graph showing a variation of pressure during the proportionally assisted breath of FIG. 1.

FIG. 2 is a graph showing a variation of pressure during the proportionally assisted (NAVA mode) breath of FIG. 1. In a graph 20, a curve 22 shows a variation of the pressure measured at a mechanical ventilator or at an airway of the patient in the course of the breath of the patient receiving assist under NAVA control. The pressure is proportional to the EAdi generated by the patient until a time 24 when the EAdi reaches a peak, at a time later than the time 16 (FIG. 1) for the non-assisted breath. The pressure continues increasing slightly until a time 26 when the EAdi is reduced to 70% of its peak. Otherwise stated, the increasing inspiratory effort of the patient is met by a proportional increase in pressure from the mechanical ventilator.

Figure 3:
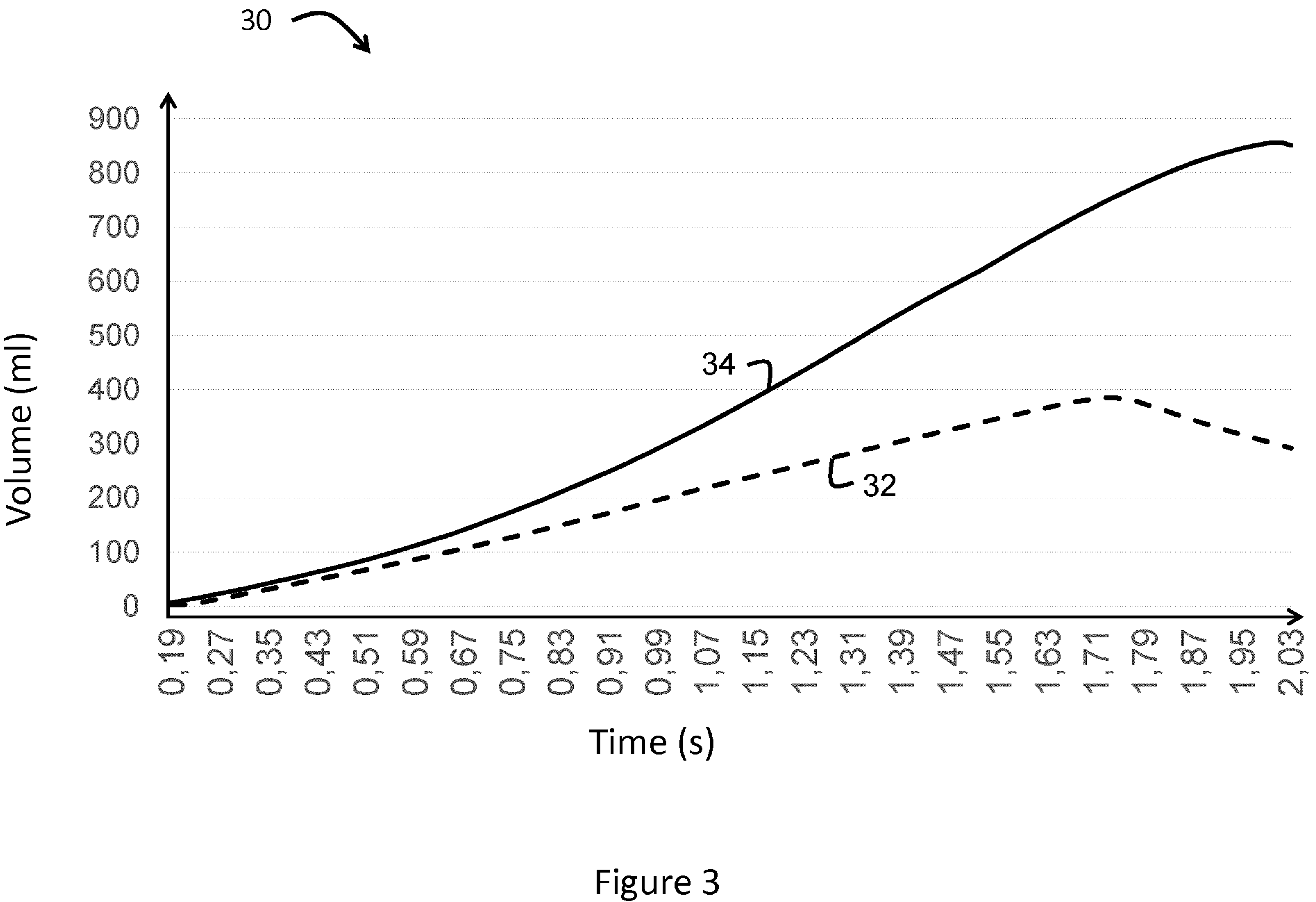
FIG. 3 is a graph showing inspiratory volumes during the non-assisted breath and during the proportionally assisted breath of FIG. 1.

FIG. 3 is a graph showing inspiratory volumes during the non-assisted breath and during the proportionally assisted breath (NAVA mode) of FIG. 1. In a graph 30, a curve 32 shows a variation of the inspiratory volume of an adult patient during the non-assisted breath while a curve 34 shows a variation of the inspiratory volume during the NAVA assisted breath for the same patient. The inspiratory volume is clearly larger when the patient is receiving NAVA assist, when compared to the inspiratory volume obtained in the non-assisted breath, even though the EAdi reveals similar inspiratory efforts, as least in the early stages of the breaths up to the time 16 of the EAdi peak.

Figure 4:
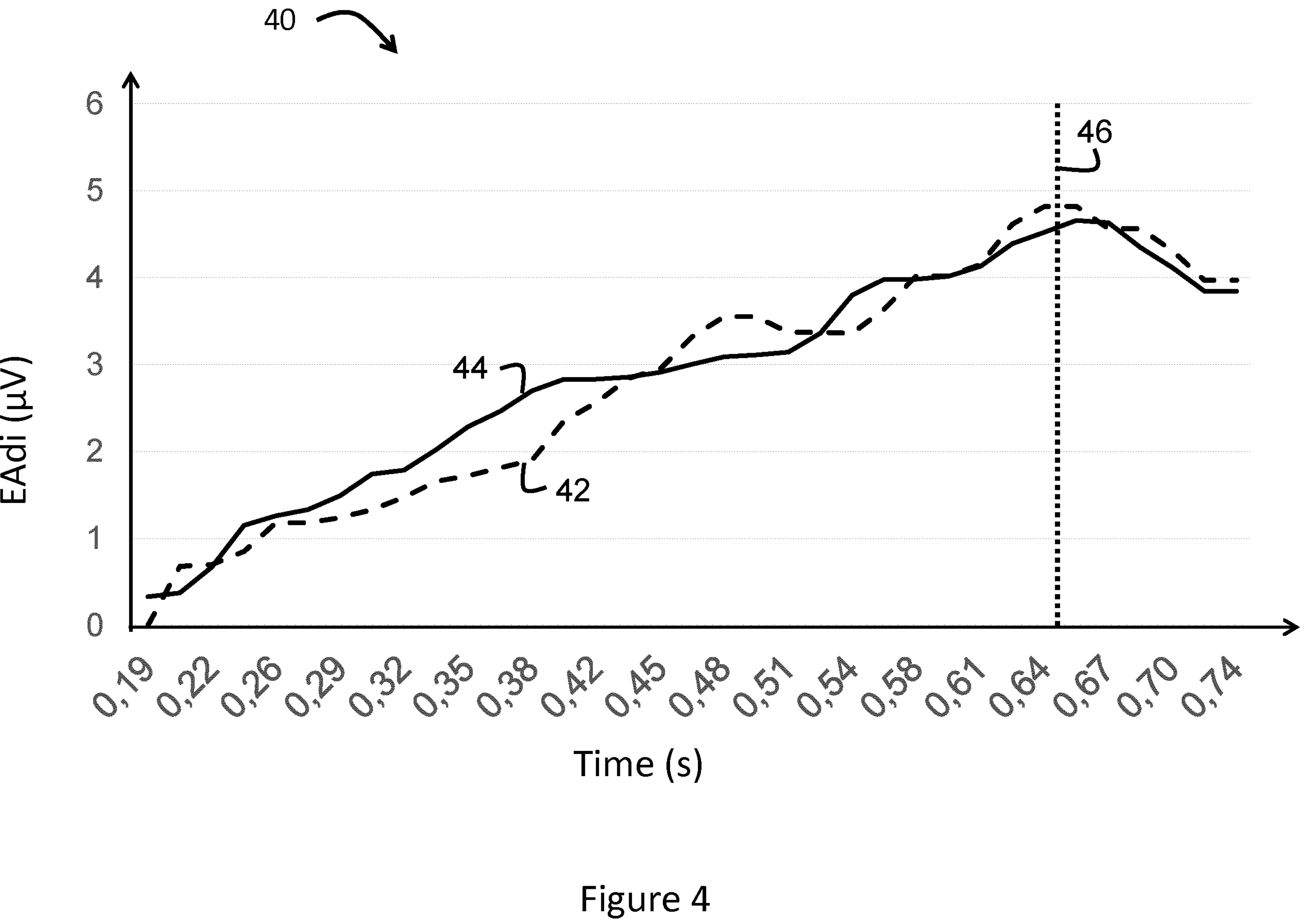
FIG. 4 is a graph showing EAdi measurements during a non-assisted breath and during a fixed-pressure assisted breath of a patient.

FIG. 4 is a graph showing EAdi measurements during a non-assisted breath and during a fixed-pressure assisted breath (PSV mode) of a patient. In a graph 40, a curve 42 shows a variation of the diaphragm electrical activity (EAdi) of the patient over time, over the course of a non-assisted breath. A curve 44 shows a variation of the diaphragm electrical activity (EAdi) of the patient over the course of breath assisted under PSV control. There is a high correlation between the curves 42 and 44, which both peak a time 46.

Figure 5:
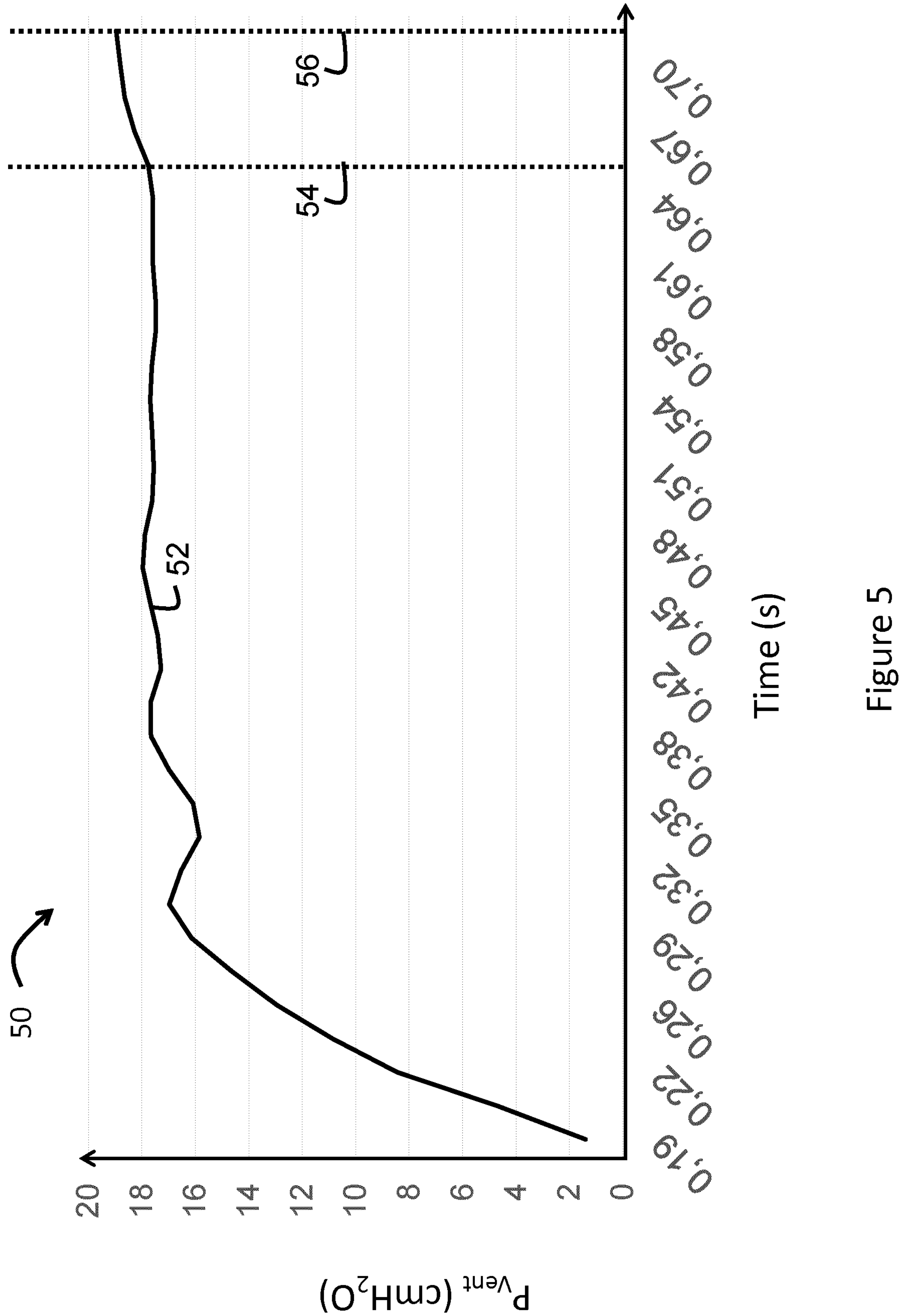
FIG. 5 is a graph showing a variation of pressure during the fixed-pressure assisted breath of FIG. 4.

FIG. 5 is a graph showing a variation of pressure during the fixed-pressure assisted breath (PSV mode) of FIG. 4. In a graph 50, a curve 52 shows a variation of the pressure measured at a mechanical ventilator or at an airway of the patient in the course of the breath of the patient receiving assist under PSV control. Considering FIGS. 4 and 5, the pressure is not proportional to the EAdi generated by the patient but reaches a plateau early in the inspiratory phase. It may be observed that the pressure does not vary significantly between a time 54 of peak EAdi and a time 56 when the EAdi is reduced to 70% of its peak.

Figure 6:
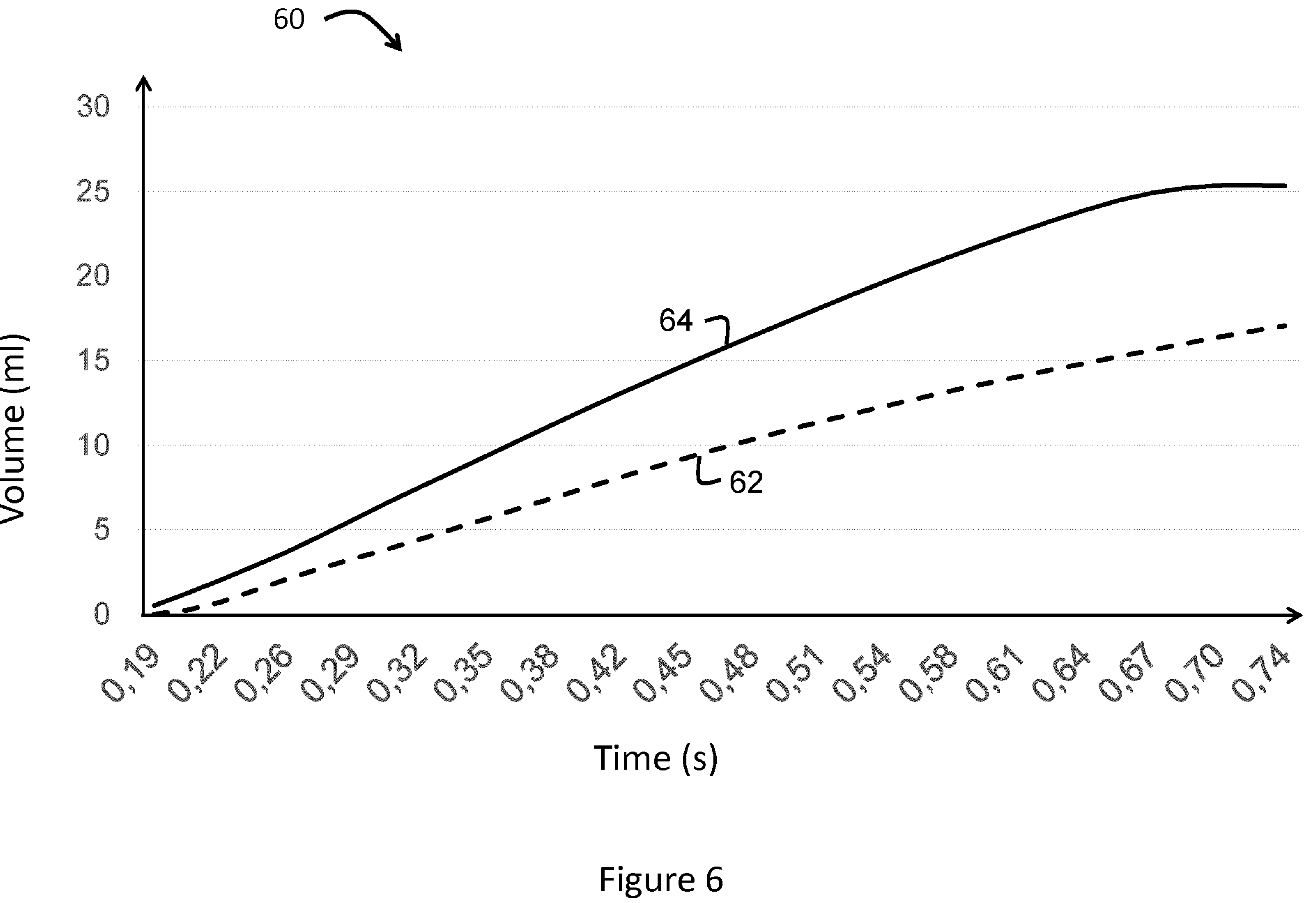
FIG. 6 is a graph showing inspiratory volumes during the non-assisted breath and during a fixed-pressure assisted breath.

FIG. 6 is a graph showing inspiratory volumes during the non-assisted breath and during the fixed-pressure assisted breath (PSV mode) of FIG. 4. In a graph 60, a curve 62 shows a variation of the inspiratory volume of a paralyzed subject during the non-assisted breath while a curve 64 shows a variation of the inspiratory volume during the PSV assisted breath of the same subject breathing spontaneously. The inspiratory volume is clearly larger when the patient is receiving PSV assist, when compared to the inspiratory volume obtained in the non-assisted breath. As in the case of FIG. 3, FIG. 6 illustrates the difference in inspiratory volumes when the subject is receiving respiratory assistance.

The following paragraphs will show how the present technology allows to correctly predict a pressure to volume relationship at high volumes, particularly at the end of the inspiratory phase of a patient, whereas earlier techniques could only predict the pressure to volume relationship at lower volumes.

FIGS. 7*a*-7*e* are a sequence diagram showing operations of a method for controlling a level of ventilatory assist applied to a patient by a mechanical ventilator. On FIGS. 7*a*-7*a*, a sequence 100 comprises a plurality of operations, some of which may be executed in variable order, some of the operations possibly being executed concurrently, some of the operations being optional. At operation 105, an electrical activity of a respiratory muscle of the patient is optionally measured during an under-assisted breath of the patient and during an assisted breath of the patient. The under-assisted breath of the patient may include a non-assisted breath, in which the mechanical ventilator provides no pressure contribution to the patient. Alternatively, the mechanical ventilator may provide some limited pressure contribution to the patient during the under-assisted breath. For example and without limitation, the mechanical ventilator may provide 50% of the pressure contribution of a 'normal assisted breath' in the course of an under-assisted breath.

In an embodiment, one or more electrical sensors may detect an electrical activity of the diaphragm of the patient, denoted EAdi. In another embodiment, one or more electrical sensors may detect an electrical activity of one or more muscles that reflect the respiratory drive of the patient. Other methods for evaluating the respiratory drive of the patient include using invasive or non-invasive sensors. For example and without limitation, the respiratory drive of the patient may be measured using surface electrodes placed on the neck and/or ribcage of the patient. Examples are provided in U.S. Pat. No. 10,517,528, issued on Dec. 18, 2019 to Sinderby et al., the disclosure of which is incorporated by reference herein. It should be understood that, in the following paragraphs, the term "EAdi" will be used for ease of illustration, without any intent to limit the present disclosure to the detection of the electrical activity of the diaphragm of the patient.

In an embodiment, operation 105 may include sub-operation 106, in which a determination is made of a time of an earliest peak of electrical activity (TimeToPeakEAdi) between the electrical activity of the respiratory muscle of the patient measured during the under-assisted breath and the electrical activity of the respiratory muscle of the patient measured during the assisted breath of the patient. The time of the earliest peak of electrical activity may correspond to the time 16 of the EAdi peak of FIG. 1, when NAVA assist is provided, or to the time 46 of the EAdi peak of FIG. 4, when PSV assist is provided.

In an embodiment, the time of the earliest peak of electrical activity between the electrical activity of the respiratory muscle of the patient measured during the under-assisted breath and the electrical activity of the respiratory muscle of the patient measured during the assisted breath of the patient is a shortest duration until a peak of electrical activity between (a) the start of the under-assisted breath of the patient and a peak of electrical activity in the under-assisted breath, and (b) the start of the assisted breath of the patient and a peak of electrical activity in the assisted breath, this shortest duration corresponding to a same value of a neural respiratory drive of the patient. Electrical activity measurements obtained during the under-assisted breath and during the assisted breath may be compared, for example and without limitation, using values regression coefficients (slope and intercept) that should remain within a predetermined range while the associated determination coefficient should exceed a certain limit. Comparison of the electrical measurements may be performed from the start of inspiration of both under-assisted and assisted breaths. Repeated regression analysis with a systematic time shift of electrical activity measurements obtained during under-assisted and assisted breaths may be performed to obtain the highest possible determination coefficient in view of maximizing a correlation of these measurements.

Instead of, or in addition to, operation 105 and sub-operation 106, the sequence may comprise operations 107, 108 and 109. At operation 107, respiratory volumes of the patient are measured over a plurality of under-assisted breaths. At operation 108, respiratory volumes of the patient are obtained over a plurality of assisted breaths. Then at operation 109, a value of the neural respiratory drive of the patient is predicted based on a statistical probability of a similar mean neural drive between the under-assisted and assisted breaths of the patient.

At operation 110 (FIG. 7*a*), a first respiratory volume of the patient during at least a part of the under-assisted breath of the patient is determined. In the embodiment that includes sub-operation 106, operation 110 may include sub-operations 111, 112 and 113. A respiratory flow of the patient is measured during the under-assisted breath at sub-operation 111. The respiratory flow of the patient is integrated during the under-assisted breath of the patient at sub-operation 112. Although the respiratory flow of the patient may be measured over the course of the entire under-assisted breath, the integration of the respiratory flow of the patient may be truncated at the time of the earliest peak of electrical activity at sub-operation 113.

At operation 115, a second respiratory volume of the patient during at least a part of the assisted breath of the patient for a duration matching the at least a part of the under-assisted breath of the patient is determined. In the embodiment that includes sub-operation 106, operation 115 may include sub-operations 116, 117 and 118. A respiratory flow of the patient is measured during the assisted breath at sub-operation 116. The respiratory flow of the patient is integrated during the assisted breath of the patient at sub-operation 117. Although the respiratory flow of the patient may be measured over the course of the entire assisted breath, the integration of the respiratory flow of the patient may be truncated at the time of the earliest peak of electrical activity at sub-operation 118.

The onset of flow for the under-assisted breath measured at sub-operation 111 and the onset of flow for the assisted breath measured at sub-operation 116 may be adjusted so that the flow measurement for the assisted breath is not delayed in relation to flow measurement for the under-assisted breath. This allows avoiding transients in later calculations.

The following operations express how the present method for controlling a level of ventilatory assist applied to a patient by a mechanical ventilator may use the detection of a peak EAdi of the patient during assisted an under-assisted breaths. Alternatively, respiratory volume measurements of the patient obtained over a sufficient number of assisted and under-assisted breaths may provide a statistical probability of a similar mean neural drive between under-assisted and assisted breaths, thereby allowing a prediction of the value of the neural respiratory drive of the patient without actually using EAdi measurements or other measurements of the patient's neural drive.

In various embodiments, a volume assistance correction is calculated at operation 120 (FIG. 7c), based on the first and second respiratory volumes. Optionally, the calculation of the volume assistance correction may be based on the first and second respiratory volumes determined using the time of the earliest peak of electrical activity.

For example and without limitation, the volume assistance correction may be calculated based on a ratio of the first and second respiratory volumes. The volume assistance correction may be calculated using volume measurements according to equation (1):

$$V_{AssitsCorr} = V_{Assist} - V_{Assist} \cdot \left(\frac{V_{NOAssist}}{V_{Assist}}\right)^n \qquad (1)$$

wherein:

$V_{AssistCorr}$ is the volume assistance correction, $V_{NoAssist}$ is the first respiratory volume of the patient measured during at least a part of the under-assisted breath of the patient, $V_{Assist}$ is the second respiratory volume of the patient measured during at least a part of the assisted breath of the patient for a duration matching the at least a part of the under-assisted breath of the patient, and n is a power factor selected from 2 and 3 when the under-assisted breath is a non-assisted breath, the value of n being lower when the under-assisted breath is a partially-assisted breath.

It is noted that parameter names introduced in equation (1) and in the following equations are used in a consistent manner throughout the present disclosure. For that reason, the description of each parameter is not repeated when they have been previously introduced.

In an embodiment where EAdi measurements are available, the volume assistance correction $V_{AssistCorr}$ may be calculated according to equation (1'):

$$V_{AssistCorr} = V_{Assist@EAdiPeak1} - V_{Assist@EAdiPeak1} \cdot \left(\frac{V_{NOAssist@EAdiPeak1}}{V_{Assist@EAdiPeak1}}\right)^n \qquad (1')$$

wherein:

$V_{NoAssist@EAdiPeak1}$ is the first respiratory volume of the patient measured from the start of the under-assisted breath of the patient until the time of the earliest peak of electrical activity, and $V_{Assist@EAdiPeak1}$ is the second respiratory volume of the patient measured from the start of the assisted breath of the patient until the time of the earliest peak of electrical activity.

Alternatively, the volume assistance correction $V_{AssistCorr}$ may be calculated using flow measurements according to equation (2):

$$V_{AssistCorr} = V_{Assist} - V_{Assist} \cdot \left(\frac{F_{NOAssist}}{F_{Assist}}\right)^n \qquad (2')$$

wherein:

$F_{NoAssist}$ is a first respiratory flow of the patient measured during at least a part of the under-assisted breath of the patient, $F_{Assist}$ is a second respiratory flow of the patient measured during at least a part of the assisted breath of the patient for a duration matching the at least a part of the under-assisted breath of the patient.

In an embodiment where EAdi measurements are available, the volume assistance correction $V_{AssistCorr}$ may be calculated according to equation (2'):

$$V_{AssistCorr} = V_{Assist@EAdiPeak1} - V_{Assist@EAdiPeak1} \cdot \left(\frac{F_{NOAssist@EAdiPeak1}}{F_{Assist@EAdiPeak1}}\right)^n \qquad (2')$$

wherein:

$F_{NoAssist@EAdiPeak1}$ is a first respiratory flow of the patient measured between the start of the under-assisted breath of the patient and the time of the earliest peak of electrical activity, and $F_{Assist@EAdiPeak1}$ is a second respiratory flow of the patient measured between the start of the assisted breath of the patient and the time of the earliest peak of electrical activity.

According to equations (1), (1'), (2) and (2'), the volume assistance correction would be zero if the volume or flow is the same during under-assisted breath and the assisted breath. In practice, this situation is not expected to occur given that the mechanical ventilator is effectively providing ventilatory assist to the patient. In these equations, the ratio of the first respiratory volume of the patient over at least a part of the assisted and under-assisted breaths, for example from the start of the under-assisted breath of the patient until the time of the earliest peak of electrical activity to the second respiratory volume of the patient from the start of the assisted breath of the patient until the time of the earliest peak of electrical activity, is raised to the power of 2 or 3. Study results have demonstrated that using the power of 3 in equations (1), (1'), (2) and (2') provides valid predictions of the transpulmonary pressure, defined as a difference between the ventilator pressure and pleural pressure.

At operation 125, a pressure is measured at the mechanical ventilator or at an airway of the patient. Optionally, the pressure may be measured at the time of the earliest peak of electrical activity.

A load of the respiratory system of the patient is calculated at operation 130 based on the volume assistance correction and on the pressure at the mechanical ventilator or at the airway of the patient. Optionally, the load of the respiratory system of the patient may be calculated based on the volume assistance correction and on the pressure at the mechanical ventilator or at the airway of the patient determined using the time of the earliest peak of electrical activity. For example and without limitation, the load of the respiratory system of the patient may be calculated according to equation (3):

$$L_{KRS} = \frac{P_{Vent}}{V_{AssistCorr}} \qquad (3)$$

wherein:

$L_{KRS}$ is the load of the respiratory system of the patient, and $P_{Vent}$ is the pressure contribution from the mechanical ventilator measured at the mechanical ventilator or at the airway of the patient.

In an embodiment where EAdi measurements are available, the load of the respiratory system of the patient $L_{KRS}$ may be calculated according to equation (3'):

$$L_{KRS} = \frac{P_{Vent@EAdiPeak1}}{V_{AssistCorr}} \tag{3'}$$

wherein:

$P_{Vent@EAdiPeak1}$ is the pressure contribution from the mechanical ventilator measured at the mechanical ventilator or at the airway of the patient at the time of the earliest peak of electrical activity.

Equations (3) and (3') are based on the volume assistance correction $V_{AssistCorr}$ calculated with the power factor n being equal to 2.

Then at operation 135, the mechanical ventilator is controlled according to the load of the respiratory system of the patient. The mechanical ventilator may be controlled so that one or more of conditions 136, 137 and/or 138 is met:

Condition 136: A target respiratory volume is delivered to the patient;

Condition 137: The electrical activity of the respiratory muscle during an assisted breath of the patient meets or exceeds a target threshold; and Condition 138: A total respiratory pressure of the patient is equal to a target respiratory pressure plus or minus a safety margin.

Embodiments of the present method for controlling a level of ventilatory assist applied to a patient by a mechanical ventilator may include some of the following operations 140 to 185, executed in view of determining a neuromechanical efficiency and a neuroventilatory efficiency of the patient, as well as a total neuromechanical efficiency and a total neuroventilatory efficiency. The neuromechanical efficiency may be described as an indication of an amount of pressure required as a function of electrical activity (EAdi or equivalent measure of the respiratory drive of the patient) to overcome a total respiratory system load. The neuroventilatory efficiency may be described as an indication of a respiratory volume obtained as a function of electrical activity.

At operation 140 (FIG. 7*d*), a third respiratory volume of the patient is determined, covering a totality of the under-assisted breath of the patient. Operation 140 may include sub-operations 141 and 142. In sub-operation 141, a respiratory flow of the patient is measured during the under-assisted breath. In sub-operation 142, the respiratory flow of the patient is integrated over the totality of the under-assisted breath of the patient.

At operation 145, a fourth respiratory volume of the patient is determined, covering a totality of the assisted breath of the patient. Operation 145 may include sub-operations 146 and 147. In sub-operation 146, a respiratory flow of the patient is measured during the assisted breath. In sub-operation 147, the respiratory flow of the patient is integrated over the totality of the assisted breath of the patient.

Figure 7A:
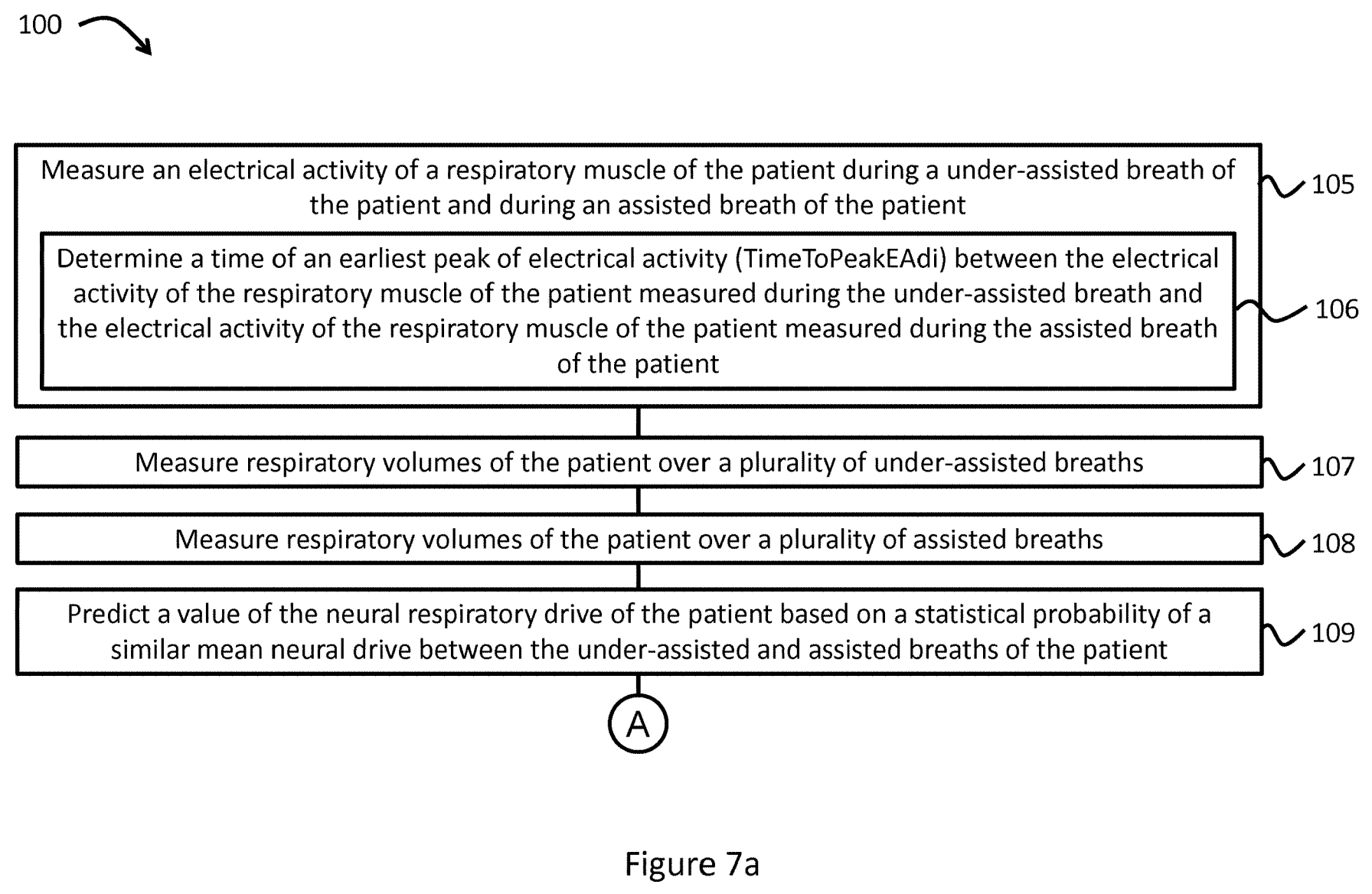
Figure 7B:
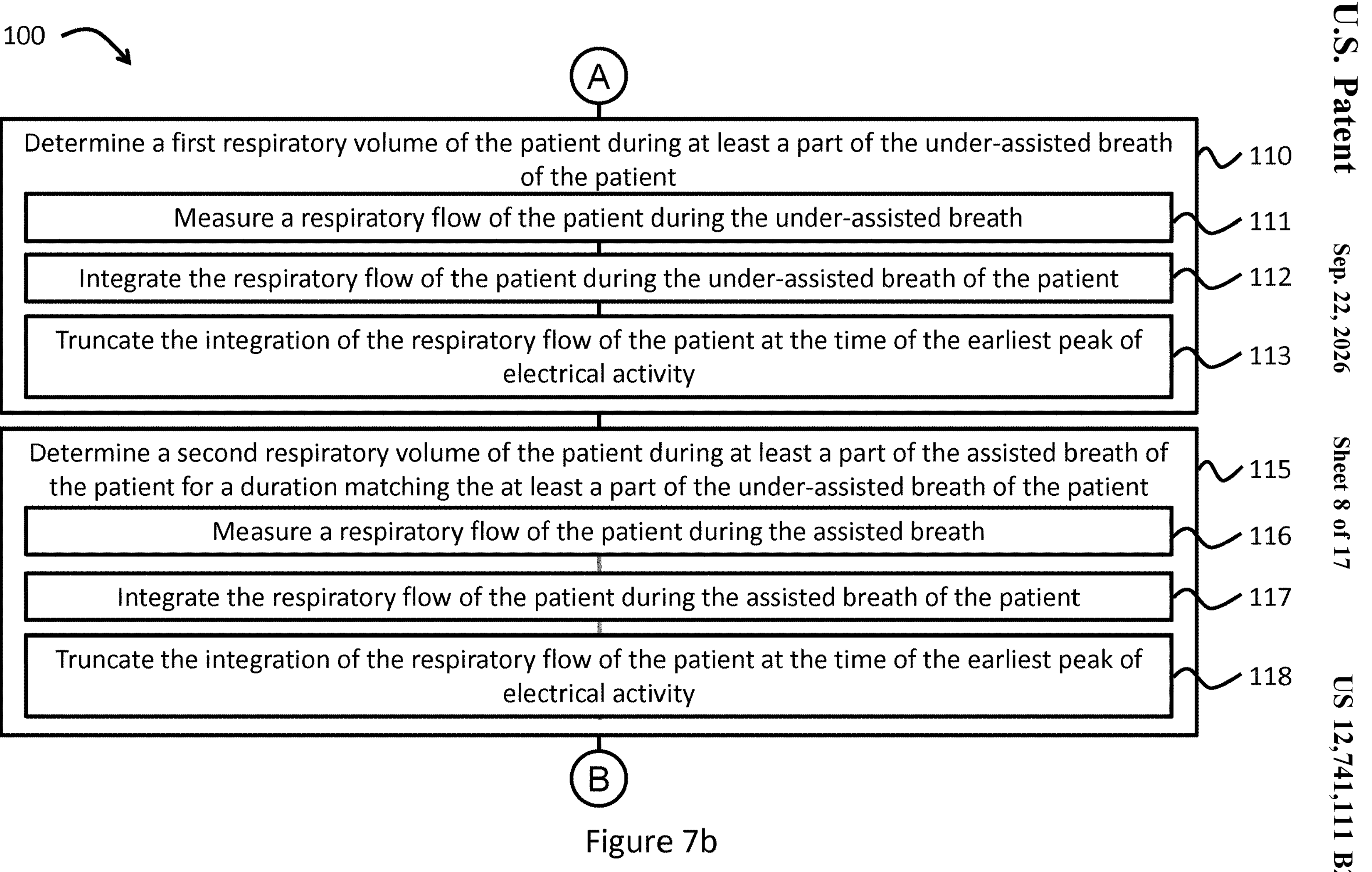
Figure 7C:
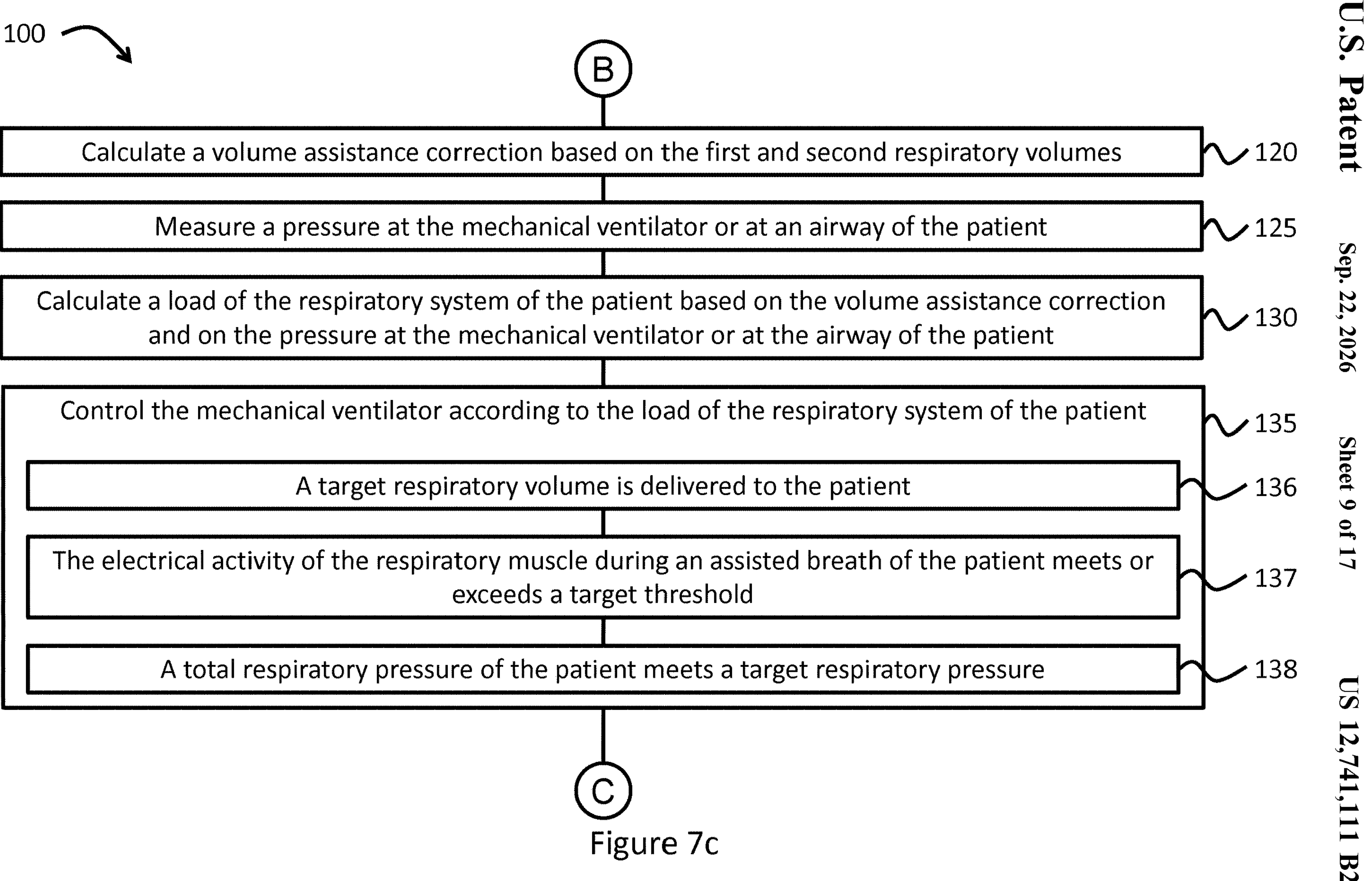
Figure 7E:
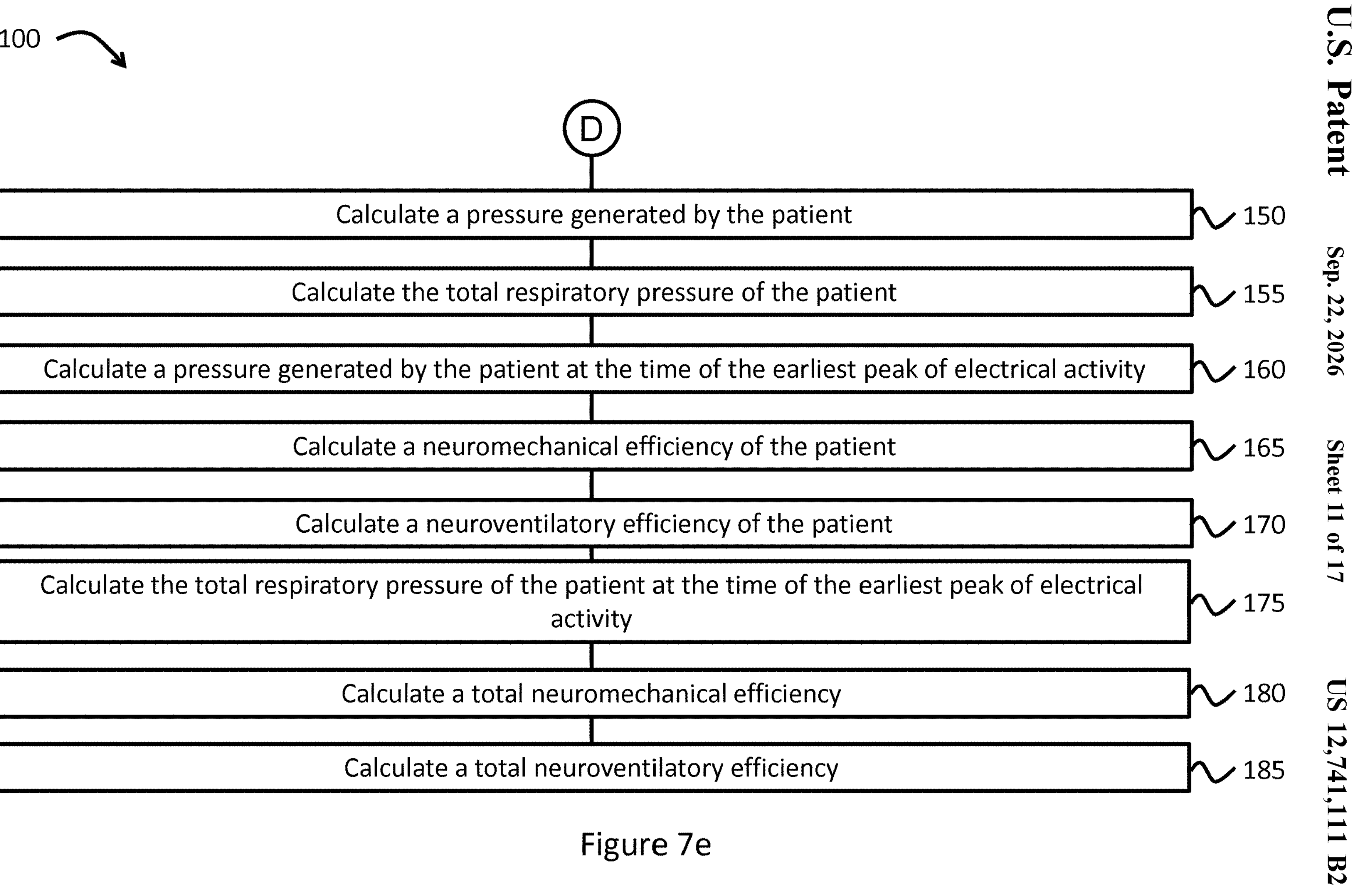

A pressure generated by the patient is calculated at operation 150 (FIG. 7*e*). The pressure generated by the patient may be calculated according to equation (4):

$$Ppat_{RS} = L_{KRS} \cdot V_{NoAssist} \cdot \left(\frac{V_{NOAssist}}{V_{Assist}}\right)^n \tag{4}$$

wherein:

$Ppat_{RS}$ is the pressure generated by the patient.

In equation (4), the power factor n is equal to 1 to reflect that the volume measurement is made considering the contribution of the patient in the absence of ventilatory assist.

The total respiratory pressure of the patient, generated both by the patient and the ventilator, may also be calculated at operation 155, according to equation (5):

$$Ptot_{RS} = L_{KRS} \cdot V_{Assist} \tag{5}$$

$Ptot_{RS}$ is the total respiratory pressure of the patient, and $V_{Assist}$ is the fourth respiratory volume of the patient in the totality of the assisted breath of the patient, determined at operation 145.

In an embodiment where EAdi measurements are available, a pressure generated by the patient at the time of the earliest peak of electrical activity may be calculated at operation 160, according to equation (6):

$$Ppat_{RS@EAdiPeak1} = L_{KRS} \cdot V_{NoAssist@EAdiPeak1} * \left(\frac{V_{NOAssist@EAdiPeak1}}{V_{Assist@EAdiPeak1}}\right)^n \tag{6}$$

wherein:

$Ppat_{RS@EAdiPeak1}$ is the pressure generated by the patient at the time of the earliest peak of electrical activity; and In equation (6), the power factor n is equal to 1 to reflect that the volume measurement is made considering the contribution of the patient in the absence of ventilatory assist.

It is observed that $Ptot_{RS}$ represents the total dynamic respiratory pressure of the patient, generated both by the patient and the ventilator. As such, the relation between $Ppat_{RS}$, $Ptot_{RS}$ and $P_{Vent}$ may also be expressed using equation (7) or (7'):

$$Ptot_{RS} = Ppat_{RS} + P_{Vent} \tag{7}$$

$$Ptot_{RS} = Ppat_{RS@EAdiPeak1} + P_{Vent@EAdiPeak1} \tag{7'}$$

The neuromechanical efficiency of the patient may then be calculated at operation 165, according to equation (8):

$$NME_{pat} = \frac{Ppat_{RS@EAdiPeak1}}{EAdi_{@EAdiPeak1}} \tag{8}$$

wherein:

$NME_{pat}$ is the neuromechanical efficiency of the patient, and $EAdi_{@EAdiPeak1}$ is the electrical activity of the respiratory muscle of the patient at the time of the earliest peak of electrical activity.

Using equation (7'), equation (8) may be modified to be expressed as equation (8'):

$$NME_{pat} = \frac{(Ptot_{RS} - P_{Vent@EAdiPeak1})}{EAdi_{@EAdiPeak1}} \cdot 1 / \left( \frac{V_{NOAssist@EAdiPeak1}}{V_{Assist@EAdiPeak1}} \right)^n \quad (8')$$

wherein:

The power factor n is equal to 1.

The neuroventilatory efficiency of the patient may also be calculated at operation 170, according to equation (9):

$$NVE_{pat} = \frac{V_{NoAssist@EAdiPeak1}}{EAdi_{@EAdiPeak1}} \quad (9)$$

wherein:

$NVE_{pat}$ is the neuroventilatory efficiency of the patient.

The total respiratory pressure of the patient at the time of the earliest peak of electrical activity may be calculated at operation 175, according to equation (10):

$$Ptot_{RS@EAdiPeak1} = L_{KRS} \cdot V_{Assist@EAdiPeak1} \quad (10)$$

wherein:

$Ptot_{RS@EAdiPeak1}$ is the total respiratory pressure of the patient, generated both by the patient and the ventilator, at the time of the earliest peak of electrical activity; and Equation (10) may also be expressed as equation (10'), when EAdi measurements are available, or (10"), otherwise:

$$Ptot_{RS@EAdiPeak1} = P_{Vent@EAdiPeak1} * 1 / \left( 1 - \left( \frac{V_{NOAssist@EAdiPeak1}}{V_{Assist@EAdiPeak1}} \right)^n \right) \quad (10')$$

$$Ptot_{RS} = P_{vent} * 1 / \left( 1 - \left( \frac{V_{NOAssist}}{V_{Assist}} \right)^n \right) \quad (10'')$$

In equations (10') and (10"), the power factor n is equal to 2.

The total neuromechanical efficiency may then be calculated at operation 180, according to equation (11):

$$NME_{tot} = \frac{Ptot_{RS@EAdiPeak1}}{EAdi_{@EAdiPeak1}} \quad (11)$$

wherein:

$NME_{tot}$ is the total neuromechanical efficiency.

The total neuroventilatory efficiency may also be calculated at operation 185, according to equation (12):

$$NVE_{tot} = \frac{V_{Assist@EAdiPeak1}}{EAdi_{@EAdiPeak1}} \quad (12)$$

wherein:

$NVE_{tot}$ is the total neuroventilatory efficiency.

According to the present disclosure, the total neuromechanical efficiency $NME_{tot}$ and the total neuroventilatory efficiency $NVE_{tot}$ may now be calculated based on actual measurements, using dynamic values for the total respiratory pressure of the patient $Ptot_{RS@EAdiPeak1}$ and for the load of the respiratory system of the patient $L_{KRS}$. The skilled reader will appreciate that earlier techniques were limited to predicting neuromechanical efficiency value based on measurements obtained during inspiratory occlusion. The $NME_{pat}$ reflects the pressure of the patient per μV of diaphragm electrical activity that is required to obtain a given respiratory volume. This and other values may be used by the controller 300 to control the mechanical ventilator 210, both in NAVA mode and in PSV mode.

In situations where a very stiff chest wall or very stiff lungs of the patient are a dominating factor, an elastic component of the total respiratory system load of the patient may exceed the $Ptot_{RS}$ value, which may then need to be adjusted. These situations may be detected when the end inspiratory pressure value of the assisted breath is in decline, after the peak of the EAdi. FIGS. 2 and 5 show examples where EAdi for the assisted breaths drops to 70% of its peak. The expression $P_{Vent@EAdis\leq70\%}$ represents a later phase of a breath starting when $P_{Vent}$ has reduced to a value corresponding to a time when the EAdi is at 70% of its peak, $P_{Vent}$ reducing further thereafter. Changes in $P_{Vent}$ after $P_{Vent@EAdis\leq70\%}$ describe the effect of the recoil of the respiratory system of the patient during relaxation of the respiratory muscles.

It is contemplated that other methods of determining post-inspiratory pressure against occluded airways may be used if EAdi is not measured.

A total corrected pressure $Ptot_{RSCorr}$ may be calculated, using relation (13):

$$\text{if } P_{Vent@EAdi\leq70\%} + RLcorr > Ptot_{RS} \text{ then } Ptot_{RSCorr} = P_{Vent@EAdi\leq70\%} + RLcorr \quad (13)$$

wherein:

RLcorr is a correction factor that represents a pressure overcoming a residual load (i.e. a resistive load) of the patient. In an embodiment, RLcorr may be calculated using equation (14):

$$RLcorr = Ptot_{RS} / V_{Assist@EAdiPeak1} / TimeToPeakEAdi \quad (14)$$

wherein:

TimeToPeakEAdi is the time spent from the start of a breath until the EAdi has reached its peak.

A ratio to correct for unaccounted elastic load compensation may be calculated using equation (15):

$$Ptot_{RSCorrRatio} = Ptot_{RSCorr} / Ptot_{RS} \quad (15)$$

The value $L_{KRS}$ may be adjusted using the value $Ptot_{RSCorrRatio}$ as a multiplication factor when the total corrected pressure $Ptot_{RSCorr}$ is greater than $Ptot_{RS}$.

In particular, a value $NAVA_{level}$ used by the controller 300 to control the mechanical ventilator 210 in NAVA mode may be calculated and set according to equation (16):

$$NAVA_{level} = \frac{TargetV_{Assist} \cdot L_{KRS}}{TargetEAdi_{@EAdiPeak1}} - NME_{pat} \quad (16)$$

In equation (16), an adequate target respiratory volume $TargetV_{Assist}$ is obtained at a comfortable target neural respiratory volume $TargetEAdi_{@EAdiPeak1}$ This calculation may be used to control the ventilator 210 in view of providing the adequate target respiratory volume.

In more details, equation (16) may be derived from other values as follows:

$$V_{Assist} = \frac{Ppat_{RS} + PVent}{L_{KRS}} \quad (16a)$$

$$V_{Assist} = \frac{EAdiPeak1 \cdot NME_{pat} + EAdiPeak1 \cdot NAVA_{level}}{L_{KRS}} \quad (16b)$$

$$V_{Assist} = \frac{EAdiPeak1 \cdot (NME_{pat} + NAVA_{level})}{L_{KRS}} \quad (16c)$$

$$\frac{V_{Assist} \cdot L_{KRS}}{EAdiPeak1} = NME_{pat} + NAVA_{level} \quad (16d)$$

$$\frac{V_{Assist} \cdot L_{KRS}}{EAdiPeak1} - NME_{pat} = NAVA_{level} \quad (16e)$$

Figure 8:
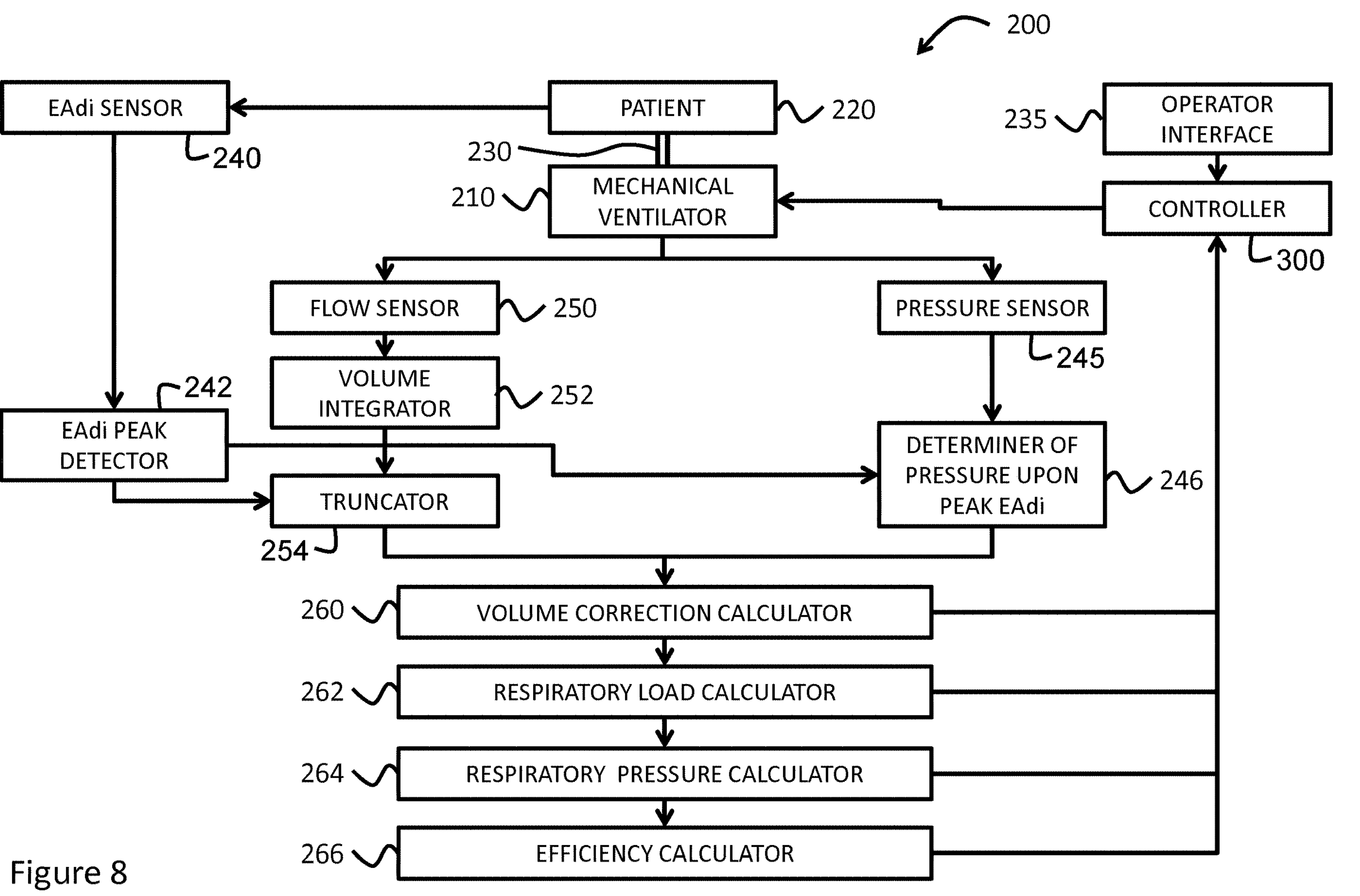
FIG. 8 block diagram of a system for controlling a level of ventilatory assist applied to a patient by a mechanical ventilator.
Figure 9:
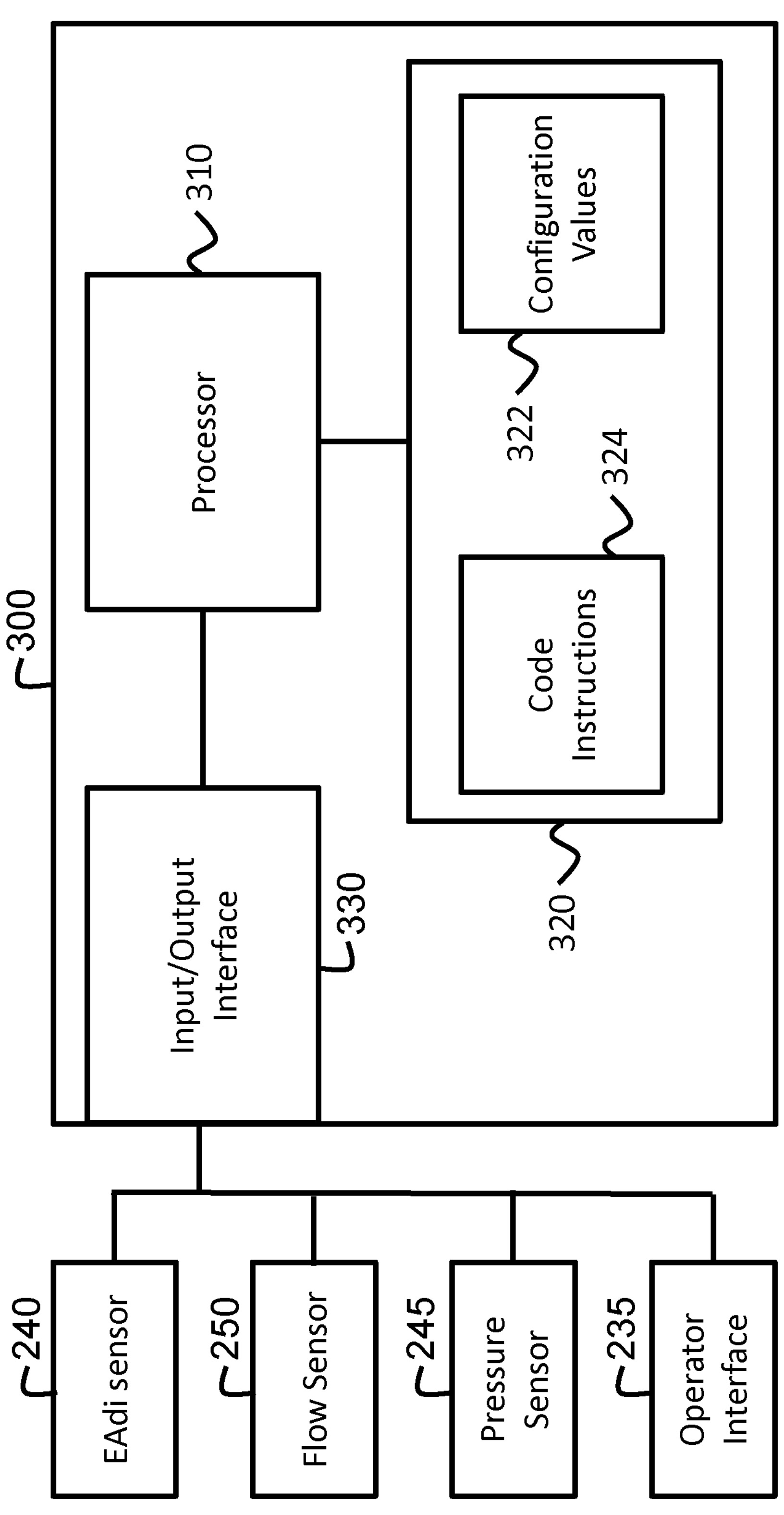
FIG. 9 is a block diagram of the controller of FIG. 8.

Each of the operations of the sequence 100 may be configured to be processed by one or more processors, the one or more processors being coupled to one or more memory devices, for example a processor and a memory device of a controller. In more details, FIG. 8 block diagram of a system for controlling a level of ventilatory assist applied to a patient by a mechanical ventilator and FIG. 9 is a block diagram of the controller of FIG. 8. Considering FIG. 8, a system 200 includes a mechanical ventilator 210 providing ventilatory assistance to a patient 220 via a tube 230, for example an endotracheal tube or a tube connected to a face mask (not shown). The mechanical ventilator 210 may be controlled in PSV mode or in NAVA mode, or in both modes, depending on the embodiment. The particular manner in which the tube 230 is connected to the patient 220 does not limit the present disclosure. Examples of manners of connecting the tube 230 to the patient 220 are shown in Sinderby'560. The mechanical ventilator 210 is controlled by a controller 300, which is presented in more details in the description of FIG. 9. 300 may be integrated in the mechanical ventilator 210 or may be a separate unit.

Various embodiments of the controller 300 may be configured to control the mechanical ventilator 210 in one or both of the NAVA and PSV modes, depending on the needs of the patient 210. The PSV mode synchronizes the operation of the mechanical ventilator 210 with inspiratory efforts of the patient 220. The NAVA mode not only synchronizes the operation of the mechanical ventilator 210 with inspiratory efforts of the patient 220, but also controls the mechanical ventilator 210 to deliver positive assist pressure in proportion to electrical activity of a respiratory muscle of the patient 220, for example and without limitation the diaphragm electrical activity (EAdi). Specifically, the magnitude of the pressure assist supplied by the mechanical ventilator 210 to the patient 220 is adjusted by a gain factor that converts the EAdi into an assist pressure level. This gain factor is the so-called NAVA level.

PSV typically delivers a fixed level of pressure throughout the inspiration; hence it is not proportional to inspiratory efforts of the patient 220. In the system 200, the PSV assist is synchronized to the inspiratory efforts of the patient 220 using an EAdi based algorithm that triggers the PSV assist on an increase in EAdi and terminates the assist on a relative level of decrease in the EAdi from its peak. A description of the neural trigger of mechanical ventilatory assist mode as described in U.S. Pat. No. 6,588,423 B1, issued on Jul. 8, 2003 to Sinderby, the disclosure of which is incorporated by reference herein.

The controller 300 receives various configuration parameters from an operator interface 235. The controller 300 is operatively connected to a plurality of sensors and may control operation of the sensors. In turn, the sensors detect various operational conditions of the mechanical ventilator 210 and/or of the patient 220 and provide measurements that are directly or indirectly used by the controller 300 to control operation of the mechanical ventilator 210.

One such sensor, for example an EAdi sensor 240, detects a respiratory drive of the patient 220. For example and without limitation, the EAdi detector 240 described in Sinderby'560 may comprise an array of electrodes mounted on an esophageal catheter passing through the center of the patient's diaphragm depolarizing region. The position of the center of the patient's diaphragm depolarizing region is determined through detection of a reversal of polarity of the electromyographic component of the electrode-detected electromyographic signals. First and second electromyographic signals detected by the electrodes of the array on opposite sides of the patient's diaphragm depolarizing region are subtracted from each other, this subtraction cancelling the noise components of the first and second electromyographic signals but adding the respective electromyographic components of these first and second signals together to produce an electromyographic signal (the EAdi signal) having an improved signal-to-noise ratio, having a reduced electrode-position-induced filter effect, and being representative of a demand to inspire from the patient's brain.

It should be noted that other sensors may detect the electrical activity of other muscles that are synchronized with inspiratory efforts of the patient 220. As mentioned earlier, the term "EAdi" is used for simplicity to represent the respiratory drive of the patient, without loss of generality of the present disclosure.

Regardless of the particular technology used to detect the respiratory drive of the patient 220, an EAdi peak detector 242 detects the time of the EAdi peak in each breath of the patient.

A pressure sensor 245 measures a pressure contribution from the mechanical ventilator 210 at the mechanical ventilator 210 or in the airway of the patient 220. A determiner of pressure upon peak EAdi 246 uses the detection from the EAdi peak detector 242 to evaluate the pressure contribution from the mechanical ventilator at the mechanical ventilator 210 or in the airway of the patient 220 at the time of the EAdi peak. A flow sensor 250, for example a pneumotachograph, detects a respiratory flow delivered in each breath to the patient 220 by the mechanical ventilator 210. A volume integrator 252 integrates over time the respiratory flow detected by the flow sensor 250 to obtain a respiratory volume delivered in each breath to the patient 220 by the mechanical ventilator 210. It is contemplated that any known technique useful in measuring the respiratory flow of volume delivery to the patient 220 may be used instead of a pneumotachograph and an integrator. A truncator 254 uses the detection from the EAdi peak detector 242 to provide a value of the respiratory volume delivered in each given breath from the onset of inspiration until the time of the EAdi peak.

Under both NAVA and PSV, the controller 300 causes the mechanical ventilator 210 to provide assisted breaths to the patient 220 most of the time, and to provide under-assisted breaths to the patient 220 from time to time so that pressure, EAdi and flow/volume measurements may be obtained both during under-assisted breaths and assisted breaths of the patient 220.

A volume correction calculator 260 calculates a volume assistance correction based on a combination of respiratory volumes obtained during under-assisted breaths and during assisted breaths of the patient 220. For example and without limitation, the volume correction calculator 260 may calculate the volume assistance correction according to equation (1) or according to equation (2). A respiratory load calculator 262 uses the volume assistance correction calculated by the volume correction calculator 260 and the pressure measurement from the pressure sensor 245 to calculate a load of the respiratory system of the patient 220. For example and without limitation, the respiratory load calculator 262 may calculate the load of the respiratory system of the patient 220 according to equation (3). The load of the respiratory system of the patient 220 is provided by the respiratory load calculator 262 to the controller 300. In turn, the controller 300 may use the load of the respiratory system of the patient 220 to control the mechanical ventilator 210 so that at least one of the following conditions is met: (i) a target respiratory volume is delivered to the patient 220, (ii) the electrical activity of the respiratory muscle measured by the EAdi sensor 240 during an assisted breath of the patient meets or exceeds a target threshold, and/or (iii) a total respiratory pressure of the patient 220 measured by the pressure sensor 245 is substantially equal to a target respiratory pressure. In this context, the total respiratory pressure of the patient 220 should be equal to the target respiratory pressure plus or minus a safety margin.

A respiratory pressure calculator 264 may calculate a pressure generated by the patient 220, for example according to equation (4), a total respiratory pressure of the patient 220, for example according to equation (5), and may further calculate a pressure generated by the patient 220 at the time of the earliest EAdi peak according to equation (6) as well as the total respiratory pressure of the patient 220 at the time of the earliest EAdi peak according to equation (10) or (10'). These values may then be used by an efficiency calculator 266 to calculate a neuromechanical efficiency of the patient using equation (8) or (8'), a neuroventilatory efficiency of the patient using equation (9), a total neuromechanical efficiency using equation (11), and a total neuroventilatory efficiency using equation (12).

EAdi measurements may be used to synchronize termination of assist at the end of an assisted breath. This typically allows a 30% reduction of the EAdi from the peak EAdi value, without opening an expiratory valve of the mechanical ventilator 210. This respiratory drive decrease means that inspiratory muscles of the patient 220 are relaxing without air leaking from the respiratory circuit. An end-expiratory quasi-static elastic recoil pressure of the total respiratory system pressure may thus be measured. Subtraction of the quasi-static elastic recoil pressure from the total respiratory pressure of the patient ($Ptot_{RS}$) generates a measure of a dynamic resistive load that has to be overcome by the inspiratory muscles of the patient 220.

The volume correction calculator 260, the respiratory pressure calculator 264 and/or the efficiency calculator 266 may provide results of their calculations to the controller 300.

In an embodiment, one or more of the EAdi peak detector 242, the determiner of pressure upon peak EAdi 246, the volume integrator 252, the truncator 254, the volume correction calculator 260, the respiratory load calculator 264 and/or the efficiency calculator 266 may be integrated as software functions within the controller 300.

The configuration parameters provided by the operator interface 235 to the controller 300 may include the adequate target respiratory volume $TargetV_{Assist}$ and the comfortable target neural respiratory drive $TargetEAdi_{@EAdiPeak1}$.

In PSV mode, the mechanical ventilator 210 may provide a pressure $P_{vent}$ calculated according to equation (17):

$$P_{vent} = \frac{TargetV_{Assist} \cdot L_{KRS}}{TargetEAdi_{@EAdiPeak1} \cdot NME_{pat}} \tag{17}$$

In more details, equation (17) may be derived from other values as follows:

$$V_{Assist} = \frac{Ppat_{RS} + PVent}{L_{KRS}} \tag{17a}$$

$$V_{Assist} = \frac{EAdiPeak1 \cdot NME_{pat} + P_{vent}}{L_{KRS}} \tag{17b}$$

$$\frac{V_{Assist} \cdot L_{KRS}}{EAdiPeak1 \cdot NME_{pat}} = P_{vent} \tag{17c}$$

The controller 300 may control an initial operation of the mechanical ventilator 210 using the adequate target respiratory volume $TargetV_{Assist}$ and the comfortable target neural respiratory volume $TargetEAdi_{@EAdiPeak1}$, both in NAVA mode and in PSV mode. The controller 300 may implement a recurring sequence, each instance of the sequence comprising controlling the mechanical ventilator 210 for at least one under-assisted breath and for a plurality of assisted breaths. The controller 300 may recalculate or cause to recalculate, following each instance of the sequence, the load of the respiratory system of the patient 220 using EAdi measurements, respiratory volume determinations and pressure measurements obtained in the course of the sequence. The controller 300 may modify control of the mechanical ventilator 210 according to the recalculated load of the respiratory system of the patient.

Other configuration parameters provided by the operator interface 235 to the controller 300 may comprise various inclusion criteria that the controller 300 or the sensors may use to accept or ignore EAdi, flow or pressure measurements or to accept or ignore volume determinations. The controller may ignore measurements obtained during a given assisted or under-assisted breath when recalculating the load of the respiratory system of the patient 220 when at least one of the inclusion criteria is not met.

In more details, in a non-limiting embodiment, the EAdi sensor 240 of the controller 300 evaluates the quality of the obtained under-assisted and assisted breaths to exclude measurements that fail to meet some inclusion criteria. The criteria may include, for example, that for either breath a target limit should be exceeded for a neural inspiration time determined as a duration of the EAdi signal, a time to reach to shortest peak EAdi, and a minimum EAdi amplitude. In the same or another non-limiting embodiment, the flow sensor 250, the volume integrator 252 or the controller 300 evaluates the quality of the obtained under-assisted and assisted breaths to exclude measurements that fail to meet some inclusion criteria. The criteria may include, for example, that for either breath a target limit should be exceeded for a flow or a volume. The flow and volume of the assisted breath should be greater than the flow and volume of the under-assisted at a certain fraction of the inspiration phase. This may be done by searching for a lack of difference in volume or flow starting from the earliest peak in EAdi of the compared assisted and under-assisted breaths, then continuing towards the onset of assist until volume or flow difference diminishes. The duration of the period where assisted volume exceeds under-assisted may be expressed in relative units of neural inspiratory time. In the same or still another embodiment, the pressure sensor 245 or the controller 300 evaluates the quality of the obtained under-assisted and assisted breaths to exclude measurements that fail to meet some inclusion criteria. The criteria may include, for example, that a lower pressure threshold should be exceed for either breaths. Also, a comparator may verify that the measured pressure actually matches the target pressures. In NAVA, a calculation of the EAdi times a NAVA level, with the eventual addition of positive end-inspiratory pressure, should match the pressure measured by the pressure sensor 245. During PSV the set target pressure limit, with the eventual addition of positive end-expiratory pressure, should match the pressure measured by the pressure sensor 245. Any model for absolute or relative comparison may be applied to validate differences between expected and observed pressures.

In a scenario where a patient discontinues spontaneous respiratory effort, the back-up mode for a conventional synchronized ventilatory assist system would rely on an arbitrarily chosen respiratory rate and assist. Based on information from the present disclosure, the total pressure for attaining adequate volumes for the patient may be measured and stored in a memory of the controller 300, along with as the neural respiratory rate. Hence, this information may be regularly updated in the memory of the controller 300 and may be used to calculate a spontaneous breathing predictor based on the calculated load of the respiratory system of the patient, this predictor being useful to re-adapt the settings of the back-up mode in order to better meet the ventilatory needs of the patient.

Turning now to FIG. 9, the controller 300 comprises a processor or a plurality of cooperating processors (represented as a processor 310 for simplicity), a memory device or a plurality of memory devices (represented as a memory device 320 for simplicity), an input/output device or a plurality of input/output devices (represented as an input/output device 330 for simplicity). Separate input devices and output devices (not shown) may be present instead of the input/output device 330. The processor 310 is operatively connected to the memory device 320 and to the input/output device 330. The memory device 320 includes a storage 322 for storing parameters, including for example the above-mentioned configuration parameters received from the operator interface 235, as well as the above-mentioned information usable to re-adapt the setting of the back-up mode of the ventilatory assist system according to a spontaneous breathing prediction for a patient who is not spontaneously breathing, the prediction being calculated by the processor 310 based on the calculated load of the respiratory system of the patient. The memory device 320 may comprise a non-transitory computer-readable medium 324 for storing instructions that are executable by the processor 310 to execute the operations of the sequence 100.

Figure 10:
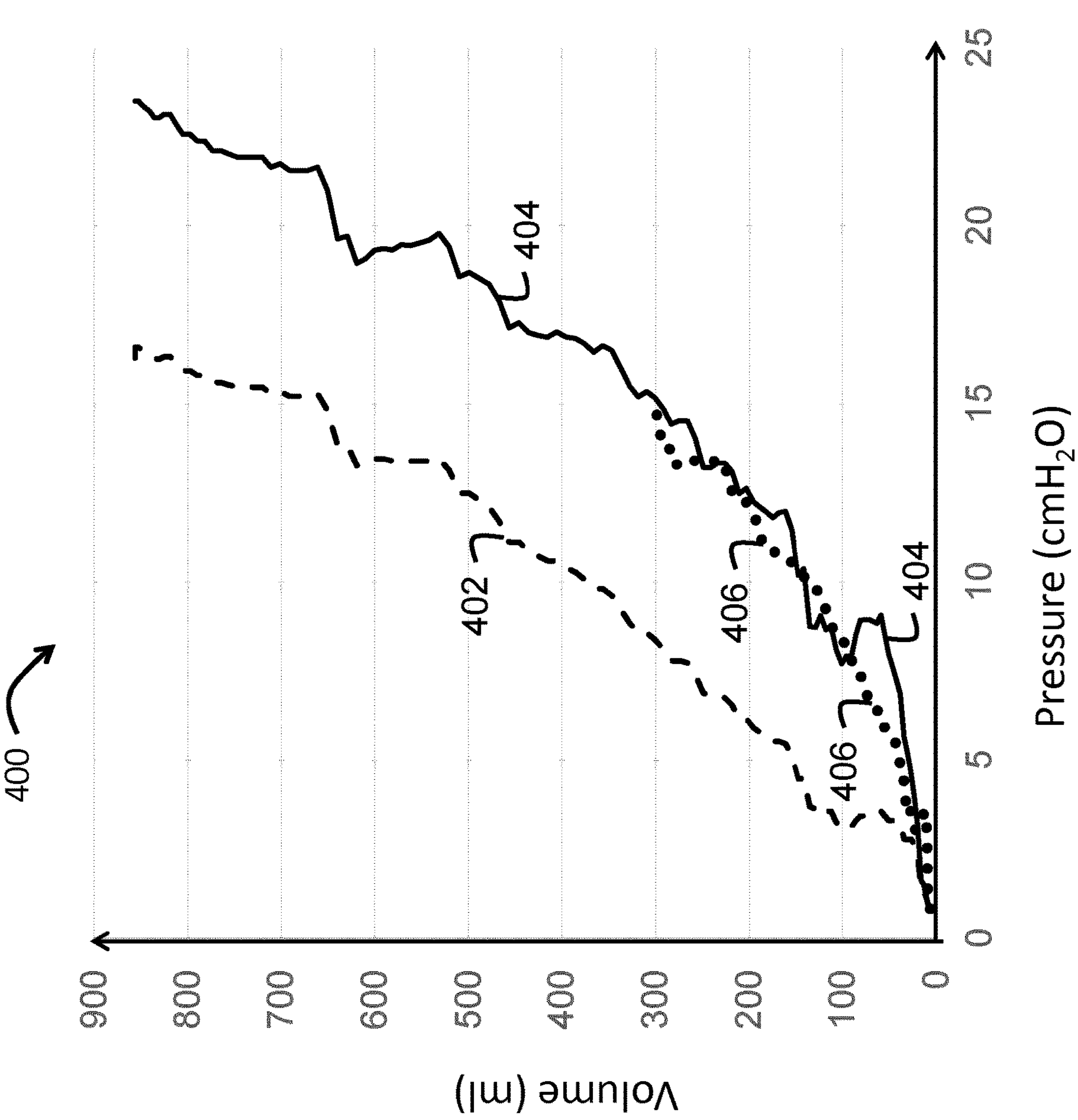
FIG. 10 is a graph comparing a mechanical pressure to volume contribution and a total respiratory pressure to volume with results obtained in Sinderby'017 during a neurally assisted breath.

FIG. 10 is a graph comparing a mechanical pressure to volume contribution and a total respiratory pressure to volume with results obtained in Sinderby'017 during a neurally assisted breath (NAVA mode). In a graph 400, a curve 402 shows a pressure assist from the mechanical ventilator 210, a curve 404 shows the total respiratory pressure of the patient ($Ptot_{RS}$), calculated using equation (1) or (2), in which n is set to a power of 2, and a curve 406 shows a total pressure calculated according to the method described in Sinderby'017. Note that the $Ptot_{RS}$ and the results obtained using the method described in Sinderby'017 show similar volume to pressure relationships at lower volume and pressure values, the present technology extending the range of the method described in Sinderby'017 to much higher volume and pressure values. Data in the graph 400 corresponds to FIGS. 1, 2 and 3.

Figure 11:
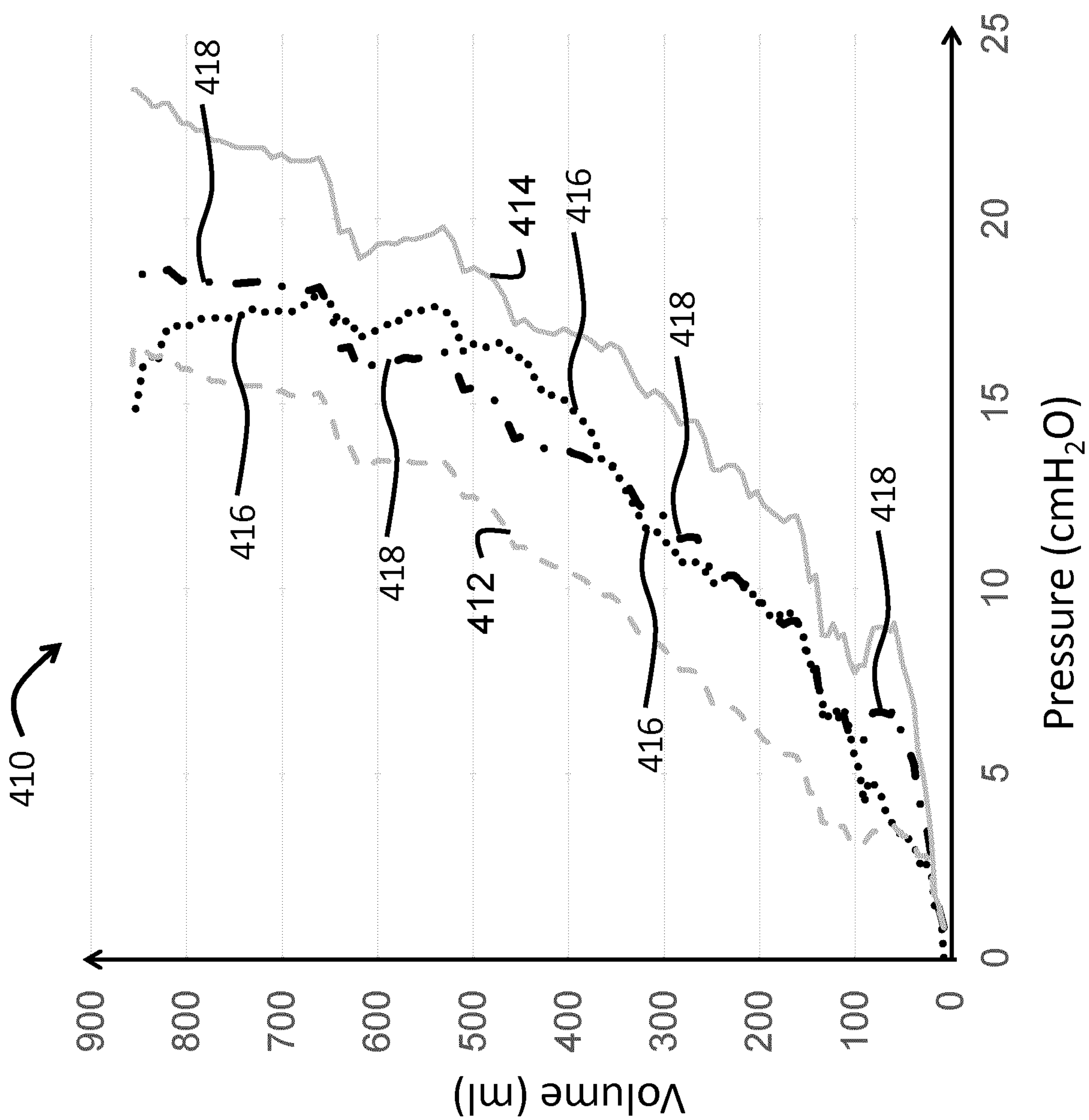
FIG. 11 is a graph showing the mechanical pressure to volume contribution, the total respiratory pressure to volume, and two variants of calculated transpulmonary pressure to volume during the neurally assisted breath of FIG. 10.

FIG. 11 is a graph showing the mechanical pressure to volume contribution, the total respiratory pressure to volume, and two variants of calculated transpulmonary pressure to volume during the neurally assisted breath (NAVA mode) of FIG. 10. In a graph 410, curves 412 and 414 are identical to curves 402 and 404 of FIG. 10. A curve 416 shows a measured transpulmonary pressure calculated as a difference between a pressure contribution from the ventilator and esophageal pressure. While the curve 416 shows a measured transpulmonary pressure of the patient, a curve 418 shows a predicted transpulmonary pressure of the patient obtained using equations (1) or (2) in which the power factor is equal to 3. It may be observed that curves 416 and 418 representing the measured and predicted transpulmonary pressure of the patient, respectively, appear between the curves 412 and 414 that represent the pressure assist from the mechanical ventilator 210 and the total respiratory pressure of the patient ($Ptot_{RS}$), respectively. Curves 416 and 418 show similar pressure to volume relationships. Data in the graph 400 corresponds to FIGS. 1,2 and 3.

Figure 12:
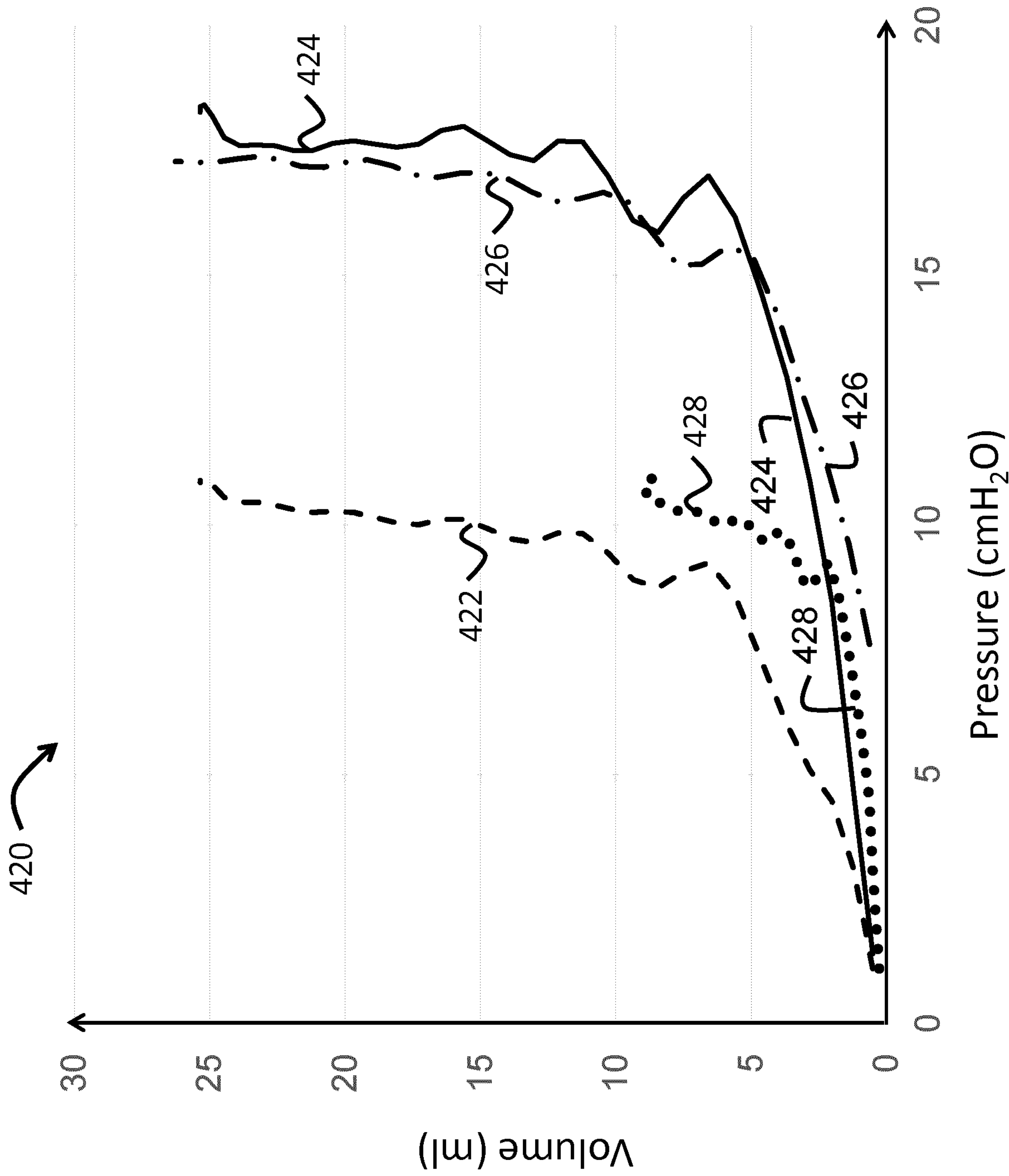
FIG. 12 is a graph comparing a mechanical pressure to volume contribution, a total respiratory pressure to volume, and a pressure to volume during pressure control ventilation during paralysis with results obtained in Sinderby'017 during a pressure assisted breath.

FIG. 12 is a graph comparing a mechanical pressure to volume contribution, a total respiratory pressure to volume, and a pressure to volume during pressure control ventilation during paralysis with results obtained in Sinderby'017 during a pressure assisted breath (PSV Mode). In a graph 420, a curve 422 FIG. 12 shows an inspiratory volume as a function of the pressure assist from the mechanical ventilator 210. A curve 424 shows the inspiratory volume as a function of the total pressure of respiratory system ($Ptot_{RS}$). A curve 426 shows the inspiratory volume as a function of the pressure measured when using PSV during paralysis. Note that there is a strong correlation between the curves 424 and 426. The pressure during PSV and paralysis reflects the entire pressure required to expand the lungs, ribcage and abdomen. It becomes possible to standardize the resistive load at a given flow rate. The curve 424 of the inspiratory volume as a function of the total pressure of respiratory system ($Ptot_{RS}$) is a good predictor for the performance of PSV, under which the assist is not proportional to patient's respiratory effort. A curve 428 shows the pressure volume relation obtained by the method described in Sinderby'017. Curve 428 does not reflect the volume to pressure relationship when PSV is used for a paralyzed patient. The present technology therefore performs better than Sinderby'017 for non-proportional ventilatory assist techniques. Data in the graph 420 correspond to FIGS. 4, 5 and 6.

Figure 13:
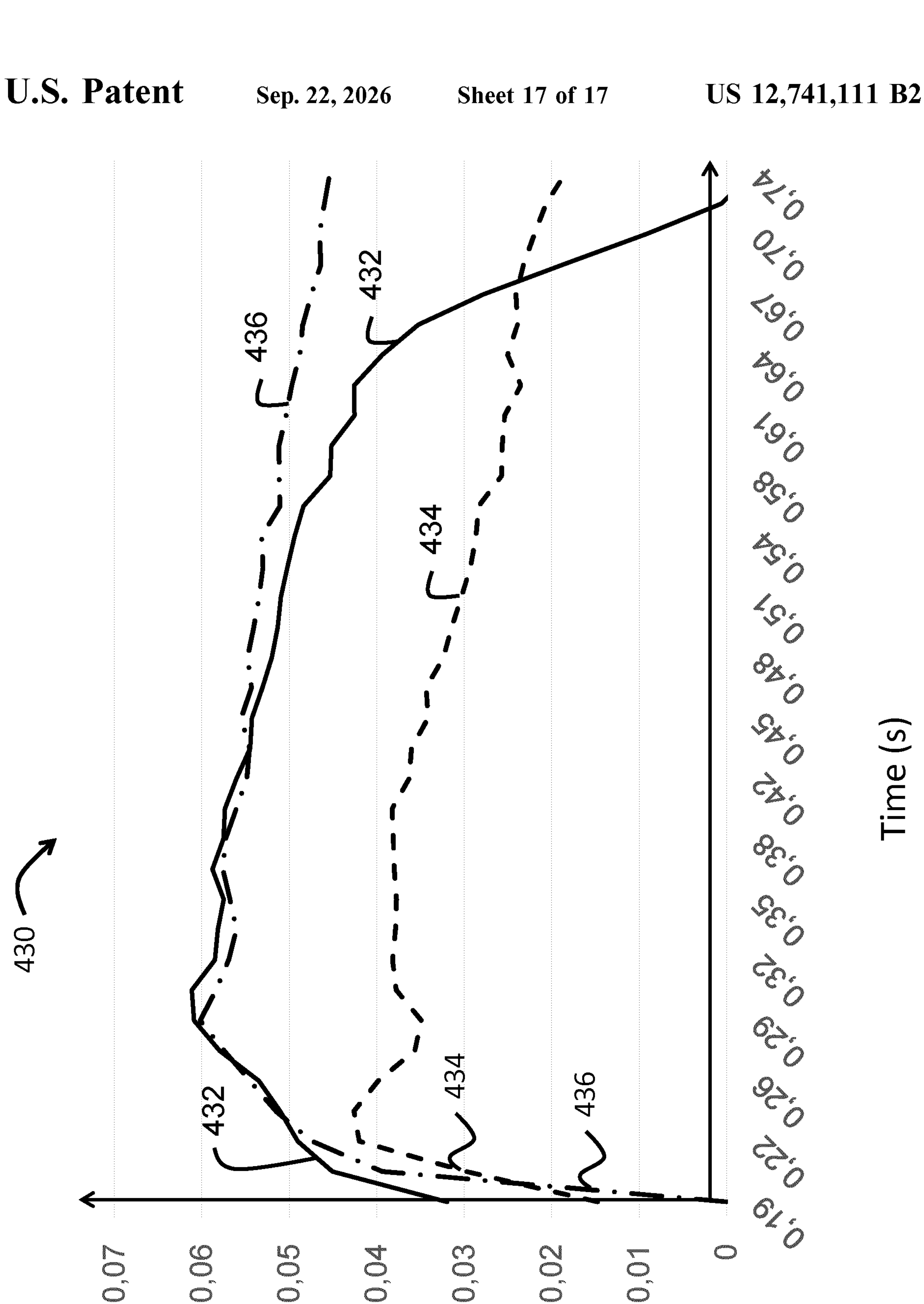
FIG. 13 is a graph showing variations of flow during the pressure assisted breaths of FIG. 12.

FIG. 13 is a graph showing variations of flow during the pressure assisted breaths of FIG. 12 (PSV mode). In a graph 430, a curve 432 illustrates an inspiratory flow over time in an assisted breath of the patient 220. A curve 434 illustrates an inspiratory flow over time in a non-assisted breath of the patient 220. A curve 436 shows an inspiratory flow over time generated by the mechanical ventilator 220 using PSV when the patient 220 is paralyzed. Data in the graph 430 correspond to FIGS. 4, 5, 6 and 12. The flow of curves 436 and 432 are well correlated. This is consistent with the strong correlation between the curves 424 and 426 of FIG. 12 and further demonstrates the accuracy of the present technology in predicting volume to pressure relationships for high pressure and volume.

Those of ordinary skill in the art will realize that the description of the method and system for controlling a level of ventilatory assist applied to a patient by a mechanical ventilator are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems related to limits to the accuracy of control of delivery assist to patients. In the interest of clarity, not all of the routine features of the implementations of the method and system are shown and described. In particular, combinations of features are not limited to those presented in the foregoing description as combinations of elements listed in the appended claims form an integral part of the present disclosure. It will, of course, be appreciated that in the development of any such actual implementation of the method and system, numerous implementation-specific decisions may need to be made in order to achieve the developer's specific goals, such as compliance with application-related, system-related, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of ventilatory assist technologies having the benefit of the present disclosure.

In accordance with the present disclosure, the components, process operations, and/or data structures described herein may be implemented using various types of operating systems, computing platforms, network devices, computer programs, and/or general-purpose machines. In addition, those of ordinary skill in the art will recognize that devices of a less general-purpose nature, such as hardwired devices, field programmable gate arrays (FPGAs), application specific integrated circuits (ASICs), or the like, may also be used. Where a method comprising a series of operations is implemented by a computer, a processor operatively connected to a memory device, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory device of servers, workstations, personal computers, computerized tablets, personal digital assistants (PDA), and other devices suitable for the purposes described herein. Software and other modules may be accessible via a local memory device, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method for controlling a level of ventilatory assist applied to a patient by a mechanical ventilator, comprising:

determining a first respiratory volume of the patient during at least a part of an under-assisted breath of the patient;

determining a second respiratory volume of the patient during at least a part of the assisted breath of the patient for a duration matching the at least a part of the under-assisted breath of the patient;

calculating a volume assistance correction based on the first and second respiratory volumes;

measuring a pressure at the mechanical ventilator or at an airway of the patient;

calculating a load of a respiratory system of the patient based on the volume assistance correction and on the pressure at the mechanical ventilator or at the airway of the patient; and controlling the mechanical ventilator according to the load of the respiratory system of the patient:

wherein the first and second respiratory volumes are measured for a same value of a neural respiratory drive of the patient; and using respiratory volume measurements of the patient obtained over a plurality of under-assisted breaths of the patient and over a plurality of assisted breaths of the patient to predict a value of the neural respiratory drive of the patient based on a statistical probability of a similar mean neural drive between the under-assisted and assisted breaths of the patient.

2. The method of claim 1, wherein the value of the neural respiratory drive of the patient is obtained by measuring an electrical activity of a respiratory muscle of the patient during an under-assisted breath of the patient and during an assisted breath of the patient.

3. The method of claim 2, wherein the mechanical ventilator is controlled according to the load of the respiratory system of the patient so that at least one of the following conditions is met:

a target respiratory volume is delivered to the patient, the electrical activity of the respiratory muscle during an assisted breath of the patient meets or exceeds a target threshold, and a total respiratory pressure of the patient is equal to a target respiratory pressure plus or minus a safety margin.

4. The method of claim 3, further comprising:

determining a time of an earliest peak of electrical activity between the electrical activity of the respiratory muscle of the patient measured during the under-assisted breath and the electrical activity of the respiratory muscle of the patient measured during the assisted breath of the patient;

wherein:

the first respiratory volume of the patient is determined from a start of the under-assisted breath of the patient until the time of the earliest peak of electrical activity;

the second respiratory volume of the patient is determined from a start of the assisted breath of the patient until the time of the earliest peak of electrical activity; and the pressure is measured at the mechanical ventilator or at the airway of the patient at the time of the earliest peak of electrical activity.

5. The method of claim 4, wherein determining the time of the earliest peak of electrical activity between the electrical activity of the respiratory muscle of the patient measured during the under-assisted breath and the electrical activity of the respiratory muscle of the patient measured during the assisted breath of the patient comprises determining a shortest duration until a peak of electrical activity between (a) the start of the under-assisted breath of the patient and a peak of electrical activity in the under-assisted breath, and (b) the start of the assisted breath of the patient and a peak of electrical activity in the assisted breath.

6. The method of claim 4, wherein the volume assistance correction is calculated based on a ratio of the first and second respiratory volumes.

7. The method of claim 6, wherein the volume assistance correction is calculated as follows:

$$V_{AssistCorr} = V_{Assist@EAdiPeak1} - V_{Assist@EAdiPeak1} \cdot \left(\frac{V_{NOAssist@EAdiPeak1}}{V_{Assist@EAdiPeak1}}\right)^n;$$

wherein:

$V_{AssistCorr}$ is the volume assistance correction, $V_{NoAssist@EAdiPeak1}$ is the first respiratory volume of the patient measured from the start of the under-assisted breath of the patient until the time of the earliest peak of electrical activity, $V_{Assist@EAdiPeak1}$ is the second respiratory volume of the patient measured from the start of the assisted breath of the patient until the time of the earliest peak of electrical activity, and n is a power factor selected from 2 and 3.

8. The method of claim 4, wherein the volume assistance correction is calculated as follows:

$$V_{AssistCorr} = V_{Assist@EAdiPeak1} - V_{Assist@EAdiPeak1} \cdot \left(\frac{F_{NOAssist@EAdiPeak1}}{F_{Assist@EAdiPeak1}}\right)^n;$$

wherein:

$V_{AssistCorr}$ is the volume assistance correction, $V_{Assist@EAdiPeak1}$ is the second respiratory volume of the patient measured from the start of the assisted breath of the patient until the time of the earliest peak of electrical activity, $F_{NoAssist@EAdiPeak1}$ is a first respiratory flow of the patient measured between the start of the under-assisted breath of the patient and the time of the earliest peak of electrical activity, $F_{Assist@EAdiPeak1}$ is a second respiratory flow of the patient measured between the start of the assisted breath of the patient and the time of the earliest peak of electrical activity, and n is a power factor selected from 2 and 3.

9. The method of claim 7, wherein the load of the respiratory system of the patient is calculated as follows:

$$L_{KRS} = \frac{P_{Vent@EAdiPeak1}}{V_{AssistCorr@EAdiPeak1}};$$

wherein:

$L_{KRS}$ is the load of the respiratory system of the patient, and $P_{vent@EAdiPeak1}$ is the pressure at the mechanical ventilator or at the airway of the patient at the time of the earliest peak of electrical activity.

10. The method of claim 9, further comprising:

determining a third respiratory volume of the patient in a totality of the under-assisted breath of the patient;

determining a fourth respiratory volume of the patient in a totality of the assisted breath of the patient;

calculating a pressure generated by the patient as follows:

$$Ppat_{RS} = L_{KRS} \cdot V_{NoAssist} \cdot \left(\frac{V_{NOAssist}}{V_{Assist}}\right)^n;$$

wherein:

$Ppat_{RS}$ is the pressure generated by the patient, $V_{NoAssist}$ is the third respiratory volume of the patient in the totality of the under-assisted breath of the patient, and n is equal to 1; and calculating the total respiratory pressure of the patient as follows;

$$Ptot_{RS} = L_{KRS} \cdot V_{Assist};$$

wherein:

$Ptot_{RS}$ is the total respiratory pressure of the patient, and $V_{Assist}$ is the fourth respiratory volume of the patient in the totality of the assisted breath of the patient.

11. The method of claim 10, wherein:

determining the third respiratory volume of the patient in the totality of the under-assisted breath of the patient comprises:

measuring a respiratory flow of the patient during the under-assisted breath, and integrating the respiratory flow of the patient in the totality of the under-assisted breath of the patient; and determining the fourth respiratory volume of the patient in a totality of the assisted breath of the patient comprises:

measuring a respiratory flow of the patient during the assisted breath, and integrating the respiratory flow of the patient in the totality of the assisted breath of the patient.

12. The method of claim 11, wherein:

determining the first respiratory volume of the patient from the start of the under-assisted breath of the patient until the time of the earliest peak of electrical activity comprises truncating the integration of the respiratory flow of the patient at the time of the earliest peak of electrical activity; and determining the second respiratory volume of the patient from the start of the assisted breath of the patient until the time of the earliest peak of electrical activity comprises truncating the integration of the respiratory flow of the patient at the time of the earliest peak of electrical activity.

13. The method of claim 11, further comprising:

calculating a pressure generated by the patient at the time of the earliest peak of electrical activity according to:

$$Ppat_{RS@EAdiPeak1} = L_{KRS} \cdot V_{NoAssist@EAdiPeak1} * \left(\frac{V_{NOAssist@EAdiPeak1}}{V_{Assist@EAdiPeak1}}\right)^n;$$

wherein:

$Ppat_{RS@EAdiPeak1}$ is the pressure generated by the patient at the time of the earliest peak of electrical activity, $V_{NoAssist@EAdiPeak1}$ is the first respiratory volume of the patient measured from the start of the under-assisted breath of the patient until the time of the earliest peak of electrical activity, $V_{Assist@EAdiPeak1}$ is the second respiratory volume of the patient measured from the start of the assisted breath of the patient until the time of the earliest peak of electrical activity, and n is equal to 1; and calculating a neuromechanical efficiency of the patient according to:

$$NME_{pat} = \frac{Ppat_{RS@EAdiPeak1}}{EAdi_{@EAdiPeak1}};$$

wherein:

$NME_{pat}$ is the neuromechanical efficiency of the patient, and $EAdi_{@EAdiPeak1}$ is the electrical activity of the respiratory muscle of the patient at the time of the earliest peak of electrical activity.

14. The method of claim 13, further comprising:

calculating a neuroventilatory efficiency of the patient according to:

$$NVE_{pat} = \frac{V_{NoAssist@EAdiPeak1}}{EAdi_{@EAdiPeak1}};$$

wherein:

$NVE_{pat}$ is the neuroventilatory efficiency of the patient.

15. The method of claim 13, further comprising:

calculating a total respiratory pressure of the patient at the time of the earliest peak of electrical activity according to:

$$Ptot_{RS@EAdiPeak1} = L_{KRS} \cdot V_{Assist@EAdiPeak1};$$

wherein:

$Ptot_{RS@EAdiPeak1}$ is the total respiratory pressure of the patient at the time of the earliest peak of electrical activity; and calculating a total neuromechanical efficiency according to:

$$NME_{tot} = \frac{Ptot_{RS@EAdiPeak1}}{EAdi_{@EAdiPeak1}};$$

wherein:

$NME_{tot}$ is the total neuromechanical efficiency.

16. The method of claim 13, further comprising:

calculating a total neuroventilatory efficiency according to:

$$NVE_{tot} = \frac{V_{Assist@EAdiPeak1}}{EAdi_{@EAdiPeak1}};$$

wherein:

$NVE_{tot}$ is the total neuroventilatory efficiency.

17. The method of claim 9, further comprising:

measuring a pressure $P_{Vent@EAdi\leq70\%}$ at the mechanical ventilator or at the airway of the patient when the electrical activity of the respiratory muscle of the patient has reduced to 70% of its peak or less;

comparing the total respiratory pressure of the patient with a sum of (i) the pressure $P_{Vent@EAd\leq70\%}$ and (ii) a correction factor RLcorr representing a pressure adapted to overcome a residual load of the patient; and in response to the sum of the pressure $P_{Vent@EAdi\leq70\%}$ and of the correction factor RLcorr being greater than the total respiratory pressure of the patient:

calculating a total corrected pressure $Ptot_{RSCorr}$ according to:

$$Ptot_{RSCorr} = P_{Vent@EAdi\leq70\%} + RLcorr,$$

calculating a ratio $Ptot_{RsCorrRatio}$ to correct for unaccounted elastic load compensation according to:

$$Ptot_{RSCorrRatio} = Ptot_{RSCorr}/Ptot_{RS}, \text{ and}$$

using the ratio $Ptot_{RSCorrRatio}$ as a multiplication factor to adjust the calculation of the load of the respiratory system of the patient.

18. The method of claim 1, wherein the mechanical ventilator is controlled according to the load of the respiratory system of the patient so that at least one of the following conditions is met:

a target respiratory volume is delivered to the patient, and a total respiratory pressure of the patient is equal to a target respiratory pressure plus or minus a safety margin.

19. The method of claim 1, wherein the volume assistance correction is calculated based on a ratio of the first and second respiratory volumes.

20. The method of claim 19, wherein the volume assistance correction is calculated as follows:

$$V_{AssistCorr} = V_{Assist} - V_{Assist} \cdot \left(\frac{V_{NOAssist}}{V_{Assist}}\right)^n;$$

wherein:

$V_{AssistCorr}$ is the volume assistance correction, $V_{NoAssist}$ is the first respiratory volume of the patient measured during the at least a part of the under-assisted breath of the patient, $V_{Assist}$ is the second respiratory volume of the patient measured during the at least a part of the assisted breath of the patient, and n is a power factor selected from 2 and 3.

21. The method of claim 19, wherein the volume assistance correction is calculated as follows:

$$V_{AssistCorr} = V_{Assist} - V_{Assist} \cdot \left(\frac{F_{NOAssist}}{V_{Assist}}\right)^n;$$

wherein:

$V_{AssistCorr}$ is the volume assistance correction, $V_{Assist}$ is the second respiratory volume of the patient measured during the at least a part of the assisted breath of the patient, $F_{NoAssist}$ is a first respiratory flow of the patient measured during the at least a part of the under-assisted breath of the patient, $F_{Assist}$ is a second respiratory flow of the patient during the at least a part of the assisted breath of the patient, and n is a power factor selected from 2 and 3.

22. The method of claim 20, wherein the load of the respiratory system of the patient is calculated as follows:

$$L_{KRS} = \frac{P_{Vent}}{V_{AssistCorr}};$$

wherein:

$L_{KRS}$ is the load of the respiratory system of the patient, and $P_{Vent}$ is the pressure at the mechanical ventilator or at the airway of the patient.

23. The method of claim 22, further comprising:

determining a third respiratory volume of the patient in a totality of the under-assisted breath of the patient;

determining a fourth respiratory volume of the patient in a totality of the assisted breath of the patient;

calculating a pressure generated by the patient as follows:

$$Ppat_{RS} = L_{KRS} \cdot V_{NoAssist} \cdot \left(\frac{V_{NOAssist}}{V_{Assist}}\right)^n;$$

wherein:

$Ppat_{RS}$ is the pressure generated by the patient, $V_{NOAssist}$ is the third respiratory volume of the patient in the totality of the under-assisted breath of the patient, $V_{Assist}$ is the fourth respiratory volume of the patient in the totality of the assisted breath of the patient, n is equal to 1; and calculating the total respiratory pressure of the patient as follows;

$$Ptot_{RS} = L_{KRS} \cdot V_{Assist};$$

wherein:

$Ptot_{RS}$ is the total respiratory pressure of the patient.

24. The method of claim 23, wherein:

determining the third respiratory volume of the patient in the totality of the under-assisted breath of the patient comprises:

measuring a respiratory flow of the patient during the under-assisted breath, and integrating the respiratory flow of the patient in the totality of the under-assisted breath of the patient; and determining the fourth respiratory volume of the patient in a totality of the assisted breath of the patient comprises:

measuring a respiratory flow of the patient during the assisted breath, and integrating the respiratory flow of the patient in the totality of the assisted breath of the patient.

25. The method of claim 1, wherein the under-assisted breath is a non-assisted breath.

26. The method of claim 1, wherein the under-assisted breath is a breath during which the mechanical ventilator provides less assist than in the assisted breath.

27. A system for controlling a level of ventilatory assist applied to a patient by a mechanical ventilator, comprising:

a determiner of a respiratory volume delivered to the patient;

a pressure sensor adapted for measuring a pressure at the mechanical ventilator or at an airway of the patient; and a controller operatively connected to the determiner of the respiratory volume, and to the pressure sensor, the controller comprising:

a processor, and a non-transitory computer-readable medium having stored thereon machine executable instructions for performing, when executed by the processor, the method according to claim 1.

28. The system of claim 27, wherein the determiner of the respiratory volume delivered to the patient comprises:

a flow meter adapted for detecting a respiratory flow of the patient; and an integrator adapted for determining the respiratory volume delivered to the patient by integrating the respiratory flow of the patient.

29. The system of claim 27, comprising the mechanical ventilator.

30. The system of claim 27, further comprising an operator interface operatively connected to the controller and adapted for providing to the controller at least one configuration parameter for controlling the mechanical ventilator.

31. The system of claim 30, wherein the controller further comprises a memory adapted to store the at least one configuration parameter.

32. The system of claim 31, wherein the at least one configuration parameter defines a range for the level of ventilatory assist applied to the patient by the mechanical ventilator, a low end of the range causing the mechanical ventilator to provide no assist to the patient, a high end of the range causing the mechanical ventilator to fulfill a totality of a ventilatory need of the patient.

33. The system of claim 31, further comprising an electrical sensor operatively connected to the controller, the electrical sensor being adapted for detecting an electrical activity of a respiratory muscle of the patient, wherein the controller is adapted to:

control an initial operation of the mechanical ventilator using the range for a level of ventilatory assist applied to the patient by the mechanical ventilator defined by the at least one configuration parameter;

implement a recurring sequence, each instance of the sequence comprising controlling the mechanical ventilator for at least one under-assisted breath and for a plurality of assisted breaths; and following each instance of the sequence:

recalculate the load of the respiratory system of the patient using electrical activity measurements of the respiratory muscle of the patient, respiratory volume determinations and pressure measurements obtained in the course of the sequence, and modify control of the mechanical ventilator according to the recalculated load of the respiratory system of the patient.

34. The system of claim 33, wherein:

the at least one configuration parameter further comprises:

an inclusion criterion for the electrical activity measurements, an inclusion criterion for respiratory volume determinations, and an inclusion criterion for pressure measurements; and the controller is further adapted for ignoring measurements obtained during a given assisted or under-assisted breath when recalculating the load of the respiratory system of the patient when at least one of the inclusion criterion is not met.

35. The system of claim 31, wherein the processor is further adapted to:

calculate a spontaneous breathing prediction for the patient based on the calculated load of the respiratory system of the patient;

store the spontaneous breathing prediction for the patient in the memory; and use the stored spontaneous breathing prediction for the patient for back-up control of the level of ventilatory assist to the patient when the patient is not spontaneous breathing.

* * * * *